United States Patent
Nelson et al.

(10) Patent No.: US 11,421,259 B2
(45) Date of Patent: Aug. 23, 2022

(54) CELL-FREE PROTEIN EXPRESSION USING ROLLING CIRCLE AMPLIFICATION PRODUCT

(71) Applicant: Global Life Sciences Solutions Operations UK Ltd, Sheffield (GB)

(72) Inventors: John Richard Nelson, Clifton Park, NY (US); Robert Scott Duthie, Schenectady, NY (US); Erik Leeming Kvam, Schenectady, NY (US); Wei Gao, Clifton Park, NY (US)

(73) Assignee: Global Life Sciences Solutions Operations UK Ltd, Sheffield (GB)

( * ) Notice: Subject to any disclaimer, the term of this patent is extended or adjusted under 35 U.S.C. 154(b) by 1027 days.

(21) Appl. No.: 16/041,734

(22) Filed: Jul. 20, 2018

(65) Prior Publication Data
US 2019/0071704 A1   Mar. 7, 2019

Related U.S. Application Data

(63) Continuation of application No. 15/145,838, filed on May 4, 2016, now Pat. No. 10,077,459.

(51) Int. Cl.
| | | |
|---|---|---|
| C12P 19/34 | (2006.01) | |
| C12P 21/00 | (2006.01) | |
| C12N 15/63 | (2006.01) | |
| C12N 15/67 | (2006.01) | |

(52) U.S. Cl.
CPC .............. *C12P 21/00* (2013.01); *C12N 15/63* (2013.01); *C12N 15/67* (2013.01); *C12Q 2531/125* (2013.01)

(58) Field of Classification Search
None
See application file for complete search history.

(56) References Cited

U.S. PATENT DOCUMENTS

| | | |
|---|---|---|
| 5,648,245 A | 7/1997 | Fire et al. |
| 5,807,717 A | 9/1998 | Joyce |
| 6,287,824 B1 | 9/2001 | Lizardi |
| 6,977,153 B2 | 12/2005 | Kumar et al. |
| 7,135,312 B2 | 11/2006 | Kool |
| 7,256,020 B2 | 8/2007 | Lyamichev et al. |
| 7,575,865 B2 | 8/2009 | Leamon et al. |
| 7,897,380 B2 | 3/2011 | Kay et al. |
| 8,715,732 B2 | 5/2014 | Luo et al. |
| 8,921,072 B2 | 12/2014 | Nelson et al. |
| 9,109,250 B2 | 8/2015 | Hill |
| 9,125,845 B2 | 9/2015 | Nelson et al. |
| 9,353,393 B2 | 5/2016 | Nelson et al. |
| 2005/0079510 A1 | 4/2005 | Berka et al. |
| 2008/0153128 A1 | 6/2008 | Kim et al. |
| 2008/0160524 A1 | 7/2008 | Ma et al. |
| 2008/0220425 A1 | 9/2008 | Ma et al. |
| 2008/0305142 A1 | 12/2008 | Chen et al. |
| 2009/0130720 A1* | 5/2009 | Nelson .................. C12Q 1/6848 435/91.2 |
| 2010/0008939 A1 | 1/2010 | Nelson et al. |
| 2017/0321239 A1 | 11/2017 | Nelson et al. |

FOREIGN PATENT DOCUMENTS

| | | | |
|---|---|---|---|
| CN | 101103122 A | 1/2008 | |
| CN | 104093850 A | 10/2014 | |
| CN | 106086012 A | 11/2016 | |
| WO | 2005003389 A2 | 1/2005 | |
| WO | 2006063355 A2 | 6/2006 | |
| WO | WO-2006063355 A2 * | 6/2006 | .............. A61P 31/04 |
| WO | 2007/14608 A1 | 12/2007 | |
| WO | 2013123187 A1 | 8/2013 | |
| WO | 2014189768 A1 | 11/2014 | |
| WO | WO-2014189768 A1 * | 11/2014 | ......... C12N 15/1058 |
| WO | 2016034849 A1 | 3/2016 | |
| WO | 20170191007 A1 | 11/2017 | |
| WO | 2018033730 A1 | 2/2018 | |
| WO | 2019/030155 A1 | 2/2019 | |
| WO | 2019/053039 A1 | 3/2019 | |

OTHER PUBLICATIONS

Kuhn et al., "Rolling-circle amplification under topological constraints", Nucleic Acids Research, vol. 30, Issue 2, pp. 574-580, 2001.
Kumar et al., "Cell-free protein synthesis using multiply-primed roiling circle amplification products", BioTechniques, vol. 47, Issue 1, pp. 637-639, Jul. 2009.
Carlson et al., "Cell-free protein synthesis: Applications come of age", Biotechnology Advances, 2011.
Kuhn et al., "Rolling-Circle Amplification of Duplex DNA Sequences assisted by PNA Openers", pp. 227-243, https://www.bu.edu/cab/CAB PDF/Kuhn and Demidov DNA Amplification '04.pdf.
Japanese Office Action for JP Application No. 2018-557422 dated Nov. 30, 2020 (12 pages with English translation).
Gagoski et al., "Gateway-Compatible Vectors for High-Throughput Protein Expression in Pro- and Eukaryotic Cell-Free Systems," Journal of Biotechnology, 2015, 195:1-7.
Komar et al., "Synonymous Codon Substitutions Affect Ribosome Traffic and Protein Folding During in vitro Translation," FEBS Letters 462, 1999, 387-393.

(Continued)

*Primary Examiner* — Celine X Qian
(74) *Attorney, Agent, or Firm* — Eversheds Sutherland (US) LLP

(57) ABSTRACT

Methods for in vitro transcription and translation from an RCA product are provided. The methods comprise providing a double-stranded RCA product, wherein the double-stranded RCA product consists essentially of tandem repeats of a minimalistic expression sequence. The methods further comprise expressing a protein from the double-stranded RCA product in a cell-free expression system.

19 Claims, 6 Drawing Sheets
Specification includes a Sequence Listing.

(56) References Cited

OTHER PUBLICATIONS

Sakatani et al., "A Transcription and Translation-Coupled DNA Replication System Using Rolling-Circle Replication," Scientific Reports, 2015, 9 pages.
PCT Search Report for PCT Application No. PC/EP2020/065980 dated Aug. 3, 2020 (17 pages).
Non-Final Office Action for U.S. Appl. No. 16/440,511 dated Jun. 8, 2021 (25 pages).
Celie et al., "Recombinant Cloning Strategies for Protein Expression," Current Opinion in Structural Biology, 2016, 38:145-154.
Grubaugh, Nathan D., et al., "Mosquitoes Transmit Unique West Nile Virus Populations during Each Feeding Episode", Cell Reports, vol. 19, Issue: 04, pp. 709-718, Apr. 25, 2017.
Weger-Lucarelli, James, et al., "Rescue and Characterization of Recombinant Virus from a New World Zika Virus Infectious Clone", Journal of Visualized Experiments, Issue: 124, pp. 01-08, Jun. 7, 2017.
Karbowniczek, Kinga, et al., "Doggybone™ DNA: an advanced platform for AAV production", Cell & Gene Therapy Insights, pp. 731-738, Nov. 16, 2017.
Aliota, Matthew T., et al., "Molecuilarly barcoded Zika virus libraries to probe in vivo evolutionary dynamics", PLOS Pathogens, pp. 01-25, Mar. 28, 2018.
Weger-Lucarelli, James, et al., "Using barcoded Zika virus to assess virus population structure in vitro and in Aedesaegypti mosquitoes", Virology, vol. 521, pp. 138-148, Jun. 8, 2018.
Kumar, et al., "Cell-free protein synthesis using multiply-primed rolling circle amplification products", Biotechniques, vol. 47:1, pp. 637-639, 2009.
Komar, et al., "Synonymous codon substitutions affect ribosome traffic and protein folding during in vitro translation", FEBS Letters, vol. 462:3, pp. 387-391, 1999.
CN 201780027641.8 First Office Action dated Jan. 5, 2022, 10 pages.
CN 201780027641.8 CN Search Report dated Dec. 28, 2021, 4 pages.

\* cited by examiner

CELL-FREE PROTEIN EXPRESSION USING ROLLING CIRCLE AMPLIFICATION PRODUCT

CROSS REFERENCE TO RELATED APPLICATIONS

This application is a continuation of U.S. patent application Ser. No. 15/145,838, filed on May 4, 2016, entitled "Cell-Free Protein Expression Using Rolling Circle Amplification Product".

SEQUENCE LISTING

The instant application contains a Sequence Listing, which has been submitted electronically in ASCII format and is hereby incorporated by reference in its entirety. Said ASCII copy, created on Nov. 17, 2018, is named 285524-3_SL.txt and is 11,160 bytes in size.

FIELD OF INVENTION

The invention generally relates to the generation of a rolling circle amplification product via rolling circle amplification of a deoxyribonucleic acid (DNA) mini-circle having a minimalistic expression sequence. It further relates to improved cell-free protein expression systems that involve in vitro transcription and translation of the rolling circle amplification product.

BACKGROUND

Cell-free protein expression provides a simple and efficient method for generating proteins without the complications of cell culture, cell engineering, or cell transfection. Cell-free systems for expressing recombinant proteins address various limitations of cell-based expression systems such as protein toxicity, protein degradation, protein aggregation and misfolding, uncontrolled post-translational modification, or negative effects of protein expression on cell growth due to sequestration of cellular machinery. Significantly higher quantities of proteins can be expressed in a shorter period of time using a cell-free protein expression system that can be employed for downstream high-throughput structural and functional analyses. Such in vitro protein expression also has significant advantages in terms of cost savings, streamlined production, easier scale-up, and simplified purification. In a cell-free protein expression system, a desired protein of interest is expressed by adding a DNA or RNA that encodes a gene of the protein of interest to a transcription-translation-competent cellular extract, and performing the transcription and/or translation of the gene of interest. The transcription and translation may be coupled in a single reaction to enable immediate translation of a newly synthesized mRNA into protein (coupled in vitro transcription-translation system or coupled transcription-translation in a cell-free system). The coupled in vitro transcription and translation generally increases the yield of expressed proteins with less time and in vitro manipulation. The immediate translation of the mRNA avoids possible adverse effects associated with mRNA degradation or misfolding.

One limitation of in vitro transcription-translation systems is that they require large quantities (generally in microgram quantities) of a DNA template. Generally, sufficient amounts of DNA can be obtained through multiple workflow steps and significant labor effort, for example, by cloning the DNA into a plasmid vector and propagating the plasmid in a host cell (e.g., *E. coli*) or by synthesizing DNA from multiple polymerase chain reactions (PCR). However, PCR is often not amenable for large-scale generation of high-quality DNA, due in part to the high mutation rate of PCR Additionally, the thermal cycling of PCR reactions is difficult to scale-up to larger reactions due to limitations on how quickly temperatures can be ramped in large volumes. Moreover. PCR products, being linear DNA sequences, may be rapidly degraded by the action of nucleases that are present in cell-free transcription-translation extracts. Further, sub-cloning of a gene of interest into a plasmid vector followed by high-scale propagation in *E. coli* through genetic selection is time-consuming and labor intensive.

Isothermal DNA amplification techniques such as rolling circle amplification (RCA) can be employed to generate large quantities of high-quality DNA with less effort, time, and expense, starting from a circular nucleic acid template. Rolling circle amplification reactions are isothermal, making scale-up to larger reaction sizes straightforward as there is no requirement for rapid heating and cooling. Rolling circle amplification generates RCA products that are tandem repeat units (concatamers) of the template nucleic acid sequence. RCA of a plasmid DNA, followed by coupled in vitro transcription and translation, is possible to generate the protein of interest. However, these plasmids are created via standard cloning methods involving genetic-selection inside a host cell such as *E. coli*. Such plasmids therefore contain many additional coding and non-coding sequences including sequences for the origin of replication (for example, oriC), antibiotic selection (for example, amp for beta-lactamase), and accessory sequences that are used for selection and/or screening plasmids in the host cells, such as lacZ, beta-galactosidase. Transcription and/or expression of these ancillary sequences are not desired, or may be considered inefficient, relative to the gene of interest that is meticulously sub-cloned into the plasmid. Consequently, PCR amplification of a gene of interest within the plasmid is often employed for cell-free protein expression.

There exists a need for improved in vitro transcription and translation systems for easy generation of desired proteins that are transcribed and translated from a DNA that is optimally free of any of the extraneous sequences and host cell contaminants, and does not require PCR synthesis. Also, it is desirable to increase the yield of cell-free protein systems using methods that are simplified and less time-consuming.

BRIEF DESCRIPTION

In some embodiments, a method for in vitro transcription and translation using RCA product is provided. The method comprises the steps of (a) providing a double-stranded rolling circle amplification (RCA) product, wherein the double-stranded RCA product consists essentially of tandem repeats of a minimalistic expression sequence, and (b) expressing a protein from the double-stranded RCA product in a cell-free expression system. The minimalistic expression sequence consists essentially of a promoter, an open reading frame, a ribosomal binding site and a translational termination sequence.

In some embodiments, a method for in vitro transcription and translation using DNA mini-circle is provided. The method comprises the steps of (a) providing a deoxyribonucleic acid (DNA) mini-circle, wherein the DNA mini-circle consists essentially of a minimalistic expression sequence, (b) generating a double-stranded rolling circle amplification (RCA) product via a rolling circle amplification of the DNA mini-circle, and (c) expressing a protein from the double-stranded RCA product in a cell-free expression system. The minimalistic expression sequence consists essentially of a promoter, an open reading frame, a ribosomal binding site and a translational termination sequence.

DRAWINGS

These and other features, aspects and advantages of the invention will become better understood when the following detailed description is read with reference to the accompanying figures.

DETAILED DESCRIPTION

Figure 1:
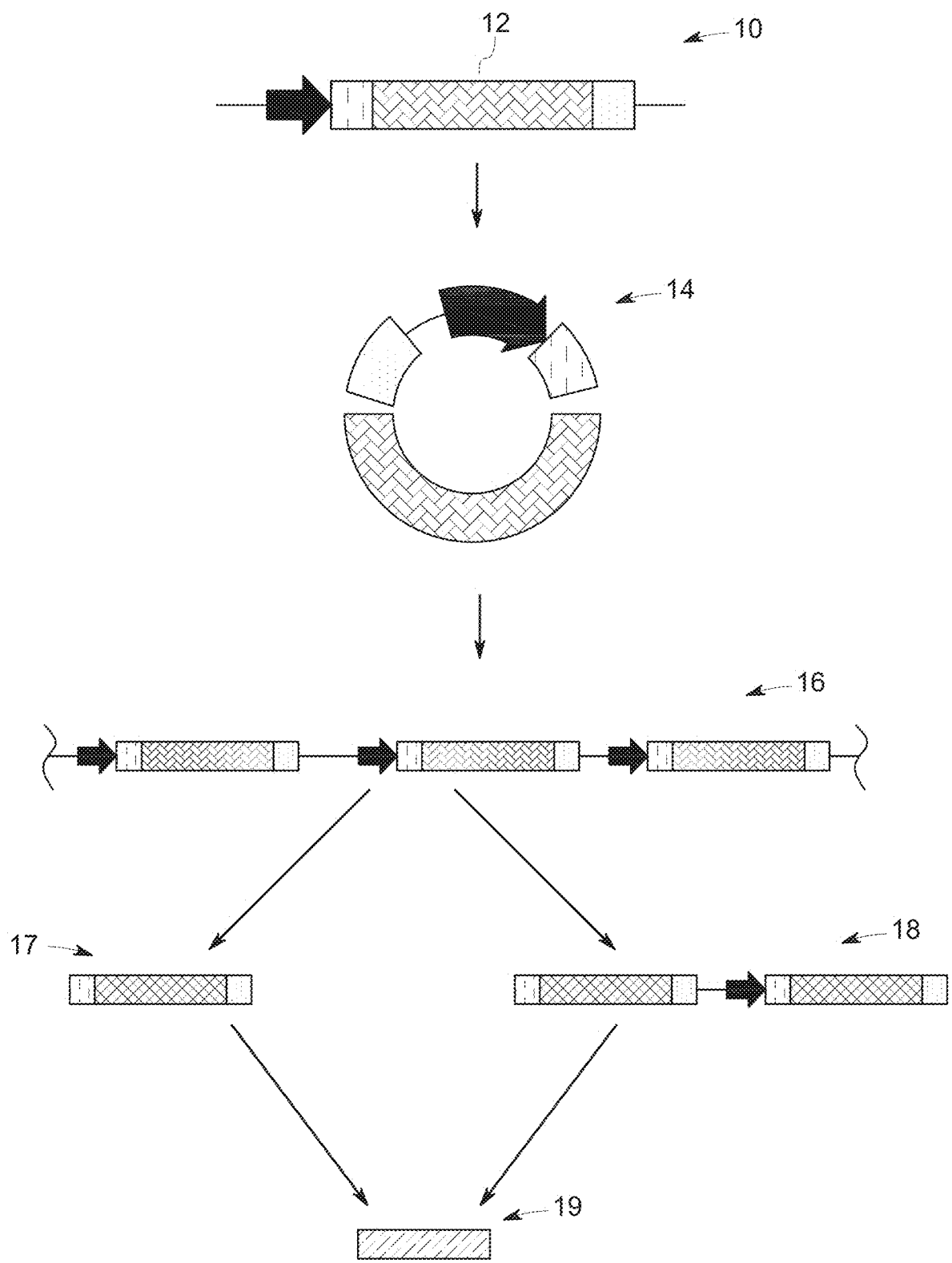
FIG. 1 illustrates a schematic representation of an embodiment of a method of in vitro transcription and translation using an RCA product derived from a mini-circle.

The following detailed description is exemplary and not intended to limit the invention or uses of the invention. Throughout the specification, exemplification of specific terms should be considered as non-limiting examples. The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. Where necessary, ranges have been supplied and those ranges are inclusive of all sub-ranges there between. To more clearly and concisely describe and point out the subject matter of the claimed invention, the following definitions are provided for specific terms, which are used in the following description and the appended claims.

As used herein, the term "nucleoside" refers to a glycosylamine compound wherein a nucleic acid base (nucleobase) is linked to a sugar moiety. A "nucleotide" refers to a nucleoside phosphate. A nucleotide may be represented using alphabetical letters (letter designation) corresponding to its nucleoside as described in Table 1. For example, A denotes adenosine (a nucleoside containing the nucleobase, adenine), C denotes cytidine. G denotes guanosine, U denotes uridine, and T denotes thymidine (5-methyl uridine). W denotes either A or T/U, and S denotes either G or C. N represents a random nucleoside, and dNTP refers to deoxyribonucleoside triphosphate. N may be any of A, C, G, or T/U.

TABLE 1

Letter designations of various nucleotides.

| Symbol Letter | Nucleotide represented by the symbol Letter |
|---|---|
| G | G |
| A | A |
| T | T |
| C | C |
| U | U |
| R | G or A |
| Y | T/U or C |
| M | A or C |
| K | G or T/U |
| S | G or C |
| W | A or T/U |
| H | A or C or T/U |
| B | G or T/U or C |
| V | G or C or A |
| D | G or A or T/U |
| N | G or A or T/U or C |

As used herein, the term "nucleotide analogue" refers to compounds that are structurally analogous to naturally occurring nucleotides. The nucleotide analogue may have an altered phosphate backbone, sugar moiety, nucleobase, or combinations thereof. Nucleotide analogues may be a natural nucleotide, a synthetic nucleotide, a modified nucleotide, or a surrogate replacement moiety (e.g., inosine). Generally, nucleotide analogues with altered nucleobases confer, among other things, different base pairing and base stacking proprieties. As used herein, the term "LNA (Locked Nucleic Acid) nucleotide" refers to a nucleotide analogue, wherein the sugar moiety of the nucleotide contains a bicyclic furanose unit locked in a ribonucleic acid (RNA)-mimicking sugar conformation. The structural change from a deoxyribonucleotide (or a ribonucleotide) to the LNA nucleotide is limited from a chemical perspective, namely the introduction of an additional linkage between carbon atoms at the 2' position and 4' position (e.g., 2'-C, 4'-C-oxymethylene linkage; see, for example, Singh, S. K., et. al., Chem. Comm., 4, 455-456, 1998, or Koshkin, A. A., et. al., Tetrahedron, 54, 3607-3630, 1998)). The 2' and 4' position of the furanose unit in the LNA nucleotide may be linked by an O-methylene (e.g., oxy-LNA: 2'-O, 4'-C-methylene-β-D-ribofuranosyl nucleotide), an S-methylene (thio-LNA), or an NH-methylene moiety (amino-LNA), and the like. Such linkages restrict the conformational freedom of the furanose ring. LNA oligonucleotides display enhanced hybridization affinity toward complementary single-stranded RNA, and complementary single- or double-stranded DNA. The LNA oligonucleotides may induce A-type (RNA-like) duplex conformations. Nucleotide analogues having altered phosphate-sugar backbone (e.g., PNA, LNA) often modify, among other things, the chain properties such as secondary structure formation. A star (*) sign preceding a letter designation denotes that the nucleotide designated by the letter is a phosphorothioate modified nucleotide. For example, *N represents a phosphorothioate modified random nucleotide. A plus (+) sign preceding a letter designation denotes that the nucleotide designated by the letter is a LNA nucleotide. For example, +A represents an adenosine LNA nucleotide, and +N represents a locked random nucleotide (i.e., a random LNA nucleotide).

As used herein, the term "oligonucleotide" refers to oligomers of nucleotides. The term "nucleic acid" as used herein refers to polymers of nucleotides. The term "sequence" as used herein refers to a nucleotide sequence of an oligonucleotide or a nucleic acid. Throughout the specification, whenever an oligonucleotide or nucleic acid is represented by a sequence of letters, the nucleotides are in 5'→3' order from left to right. For example, an oligonucleotide represented by a letter sequence $(W)_x(N)_y(S)_z$, wherein x=2, y=3 and z=1, represents an oligonucleotide sequence WWNNNS, wherein W is the 5' terminal nucleotide and S is the 3' terminal nucleotide. The oligonucleotides or nucleic acids may be a DNA, an RNA, or their analogues (e.g., phosphorothioate analogue). The oligonucleotides or nucleic acids may also include modified bases and/or backbones (e.g., modified phosphate linkage or modified sugar moiety). Non-limiting examples of synthetic backbones that confer stability and/or other advantages to the nucleic acids may include phosphorothioate linkages, peptide nucleic acid, locked nucleic acid, xylose nucleic acid, or analogues thereof.

As used herein, the term "primer" refers to a short linear oligonucleotide that hybridizes to a target nucleic acid sequence (e.g., a DNA template to be amplified) to prime a nucleic acid synthesis reaction. The primer may be an RNA oligonucleotide, a DNA oligonucleotide, or a chimeric sequence. The primer may contain natural, synthetic, or modified nucleotides. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3 nucleotides long) do not form thermodynamically stable duplexes with target nucleic acid under such hybridization conditions. The upper limit is often determined by the possibility of having a duplex formation in a region other than the pre-determined nucleic acid sequence in the target nucleic acid. Generally, suitable primer lengths are in the range of about 3 nucleotides long to about 40 nucleotides long.

As used herein, the term "random primer" refers to a mixture of primer sequences, generated by randomizing a nucleotide at any given location in an oligonucleotide sequence in such a way that the given location may consist of any of the possible nucleotides or their analogues (complete randomization). Thus the random primer is a random mixture of oligonucleotide sequences, consisting of every possible combination of nucleotides within the sequence. For example, a hexamer random primer may be represented by a sequence NNNNNN or $(N)_6$. A hexamer random DNA primer consists of every possible hexamer combinations of 4 DNA nucleotides, A, C, G and T, resulting in a random mixture comprising $4^6$ (4,096) unique hexamer DNA oligonucleotide sequences. Random primers may be effectively used to prime a nucleic acid synthesis reaction when the target nucleic acid's sequence is unknown or for performing a whole-genome amplification reaction. Random primers may also be effective in priming and producing double-stranded rolling circle amplification (RCA) product rather than single-stranded RCA product, depending on the concentration of primer.

As used herein, the term "rolling circle amplification (RCA)" refers to a nucleic acid amplification reaction that amplifies a circular nucleic acid template (e.g., single/double stranded DNA circles) via a rolling circle mechanism. Rolling circle amplification reaction is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatamers comprising tandem repeat units of the circular nucleic acid template sequence. The rolling circle amplification may be a linear RCA (LRCA), exhibiting linear amplification kinetics (e.g., RCA using a single, specific primer), or may be an exponential RCA (ERCA) exhibiting exponential amplification kinetics. Rolling circle amplification may also be performed using multiple primers (multiply primed rolling circle amplification or MPRCA) leading to hyper-branched concatamers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential amplification kinetics featuring a cascade in series of multiple-hybridization, primer-extension, and strand-displacement events involving both the primers and both strands. This often generates a discrete set of concatemeric, double-stranded nucleic acid amplification products. The RCA may be performed in vitro under isothermal conditions using a suitable nucleic acid polymerase such as Phi29 DNA polymerase. Suitable polymerases possess strand displacement DNA synthesis ability.

One or more embodiments are directed to methods for expressing a protein in a cell free expression system (e.g., an in vitro transcription and translation system). In one embodiment, the protein is expressed by in vitro transcription and translation of an RCA product that is generated by rolling circle amplification. These in vitro transcription and translation reactions yield proteins that are devoid of any intact cells. Generation of such proteins may be desired in a myriad of applications including structural and functional proteomics. The cell-free expression of such proteins may be particularly desirable for therapeutic applications.

Cell-free expression generally encompasses two modes: (1) mRNA and protein are made in a single reaction or (2) mRNA is made in a first reaction and the resulting mRNA product is added to a second, separate translation reaction. The RCA product derived from a DNA mini-circle may be utilized for either modes. (1) or (2). For example, in one embodiment, the RCA product may be provided to a "coupled in vitro transcription-translation reaction", wherein the RCA product DNA is converted to an mRNA and the mRNA is simultaneously expressed to a protein in one reaction mixture containing both the ability to produce RNA and protein. In another embodiment, the RCA product may be provided to a "linked transcription-translation reaction", wherein the RCA product DNA is first converted to mRNA and the mRNA is added separately to a translation reaction mixture to express a protein.

One or more embodiments of methods for in vitro transcription and translation from a double-stranded RCA product are provided. In one exemplary embodiment, the method includes the steps of providing a double-stranded RCA product and expressing a protein from the double-stranded RCA product in a cell-free expression system. The double-stranded RCA product consists essentially of tandem repeats of a minimalistic expression sequence, wherein the minimalistic expression sequence consists essentially of a promoter, an open reading frame, a ribosomal binding site and a translational termination sequence.

As noted, the double-stranded RCA product consists essentially of tandem repeats of a minimalistic expression sequence. The minimalistic expression sequence includes, at the minimum, a promoter, an open reading frame, a ribosomal binding site, and a translational termination sequence. It may additionally contain sequences that do not materially affect the in vitro transcription and/or translation of the RCA product. For example, it may further include sequences such as a translational enhancer sequence, an insulator sequence, or a transcriptional termination sequence. However, the minimalistic expression sequence and the resulting double stranded RCA product do not include any additional sequences that may negatively impact the in vitro transcription and translation of the RCA product. For example, the RCA product excludes any extraneous sequences, such as an origin of replication, antibiotic selection gene, or any other accessory sequences that are required for cloning, selection, screening and/or replication in a host cell. The presence of such extraneous sequences in the RCA product would materially affect the transcription and/or translation in a cell-free protein expression.

The minimalistic expression sequence is a nucleic acid sequence containing a particular gene of interest. The minimalistic expression sequence may also contain minimal genetic elements or sequences that are needed for expression (for example, a promoter sequence or enhancer sequence) of the gene of particular interest. In one or more embodiments, the minimalistic expression sequence consists essentially of a promoter, an open reading frame, a ribosomal binding site and a translational termination sequence. Numerous examples of suitable promoters are known in the art, including, for example, T7 RNA polymerase promoter sequences. Likewise, numerous examples of suitable ribosomal binding sites are known in the art, including for examples internal ribosome entry sites (IRES), polyA tracts, species-independent translational leaders (SITS), Kozak consensus sequences, and Shine-Dalgarno sequences. As noted above, the minimalistic expression sequence may additionally contain elements that do not materially affect the in vitro transcription and translation of the RCA product. For example, in some embodiments, the minimalistic expression sequence may additionally contain a translational enhancer sequence, an insulator sequence, a transcriptional termination sequence, or combinations thereof. In one embodiment of the method, the minimalistic expression sequence consists essentially of a promoter, an open reading frame, a ribosomal binding site, a translational termination sequence, and an insulator sequence. The insulator sequence generally enhances the efficiency of ribosomal binding or translational initiation. Numerous examples of suitable insulator sequences exist in the art, including for example, sequences encoding poly-histidine tracts. In some embodiments the insulator sequence may be determined empirically by inserting spacer sequences around the ribosomal binding site or by optimizing or inserting codons within the N-terminus of the expressed protein. The minimalistic expression sequence may further include a pre-promoter sequence, a sequence for protease cleavage or nucleotide cleavage, a sequence for protein purification, or combinations thereof. The minimalistic expression sequence is selected such that it does not contain any sequences that hampers or inhibits either the transcription and/or translation of the desired protein product or otherwise make the protein production more cumbersome.

In one or more embodiments, the RCA product is generated from a DNA mini-circle as a template, wherein the DNA mini-circle consists essentially of a minimalistic expression sequence. The RCA product may be a linear or a branched concatamer, wherein the concatamer contains tandem repeats of the minimalistic expression sequence derived from the DNA mini-circle. In a preferred embodiment, the RCA linear concatamer is double-stranded. As noted, the DNA mini-circle consists essentially of a minimalistic expression sequence, which means that the DNA mini-circle includes only minimalistic expression sequence and excludes any sequence other than the minimalistic expression sequence, such as any extraneous sequences. Thus, amplification of the DNA mini-circle comprising a minimalistic expression sequence may only be accomplished outside of a cell.

The "extraneous sequences" includes the sequences which are not necessary for coding or expression of a desired protein. The extraneous sequences may include the accessory sequences that are used for selection, screening, and/or propagation of a plasmid in a host cell, such as lacZ, beta-galactosidase. The extraneous sequences may include sequences for origin of replication, antibiotic selection gene, suitable restriction sites for insertion of a gene, such as multiple cloning sites, or combinations thereof. The extraneous sequence may further comprise any other sequence required for cloning into a host cell or detection in a host cell.

In one or more embodiments, the open reading frame of the minimalistic expression sequence comprises a codon-optimized sequence, a purification tag sequence, a protease cleavage site or combinations thereof. To generate a codon optimized sequence, codon bias, contextual codon preference, and/or individual codon preference are the factors which are generally considered.

The codon-optimized sequence of the open reading frame may enhance the rate or quality of translation of the RCA product. Codon optimization generally improves the protein expression by increasing the translational efficiency of a gene of interest. The functionality of a gene may also be increased by optimizing codon usage within the custom designed gene. In codon optimization embodiments, a codon of low frequency in a species may be replaced by a codon with high frequency, for example, a codon UUA of low frequency may be replaced by a codon CUG of high frequency for leucine. Codon optimization may increase mRNA stability and therefore modify the rate of protein translation or protein folding. Further, codon optimization may customize transcriptional and translational control, modify ribosome binding sites, or stabilize mRNA degradation sites.

Figure 7:
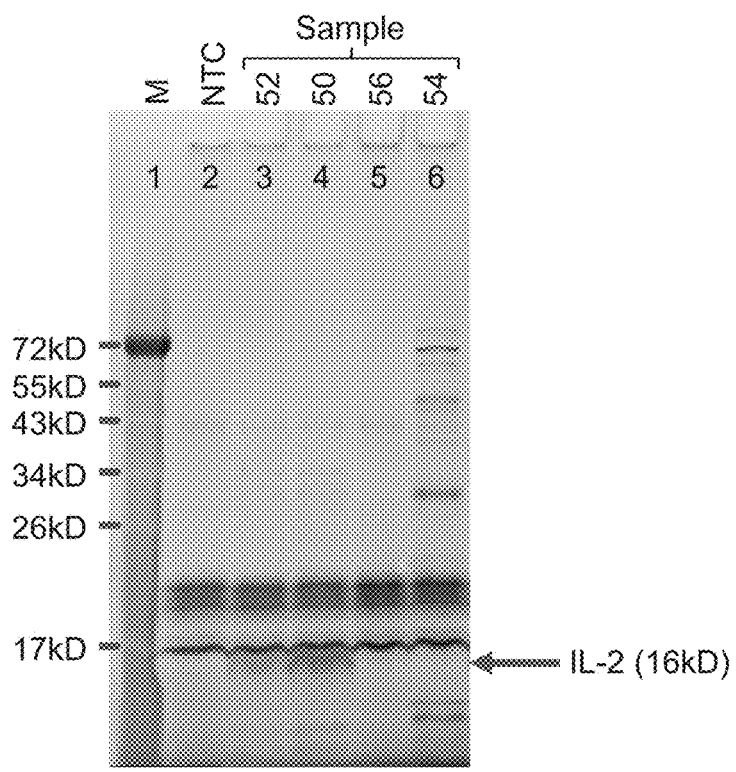
FIG. 7 depicts an SDS-PAGE gel illustrating the expression of BODIPY-labeled human interleukin 2 (IL-2, ~16 kD) by coupled in vitro transcription and translation using RCA products derived from DNA mini-circles in comparison to PCR-amplified DNA templates and a no template control (NTC) expression reaction.
Figure 8:
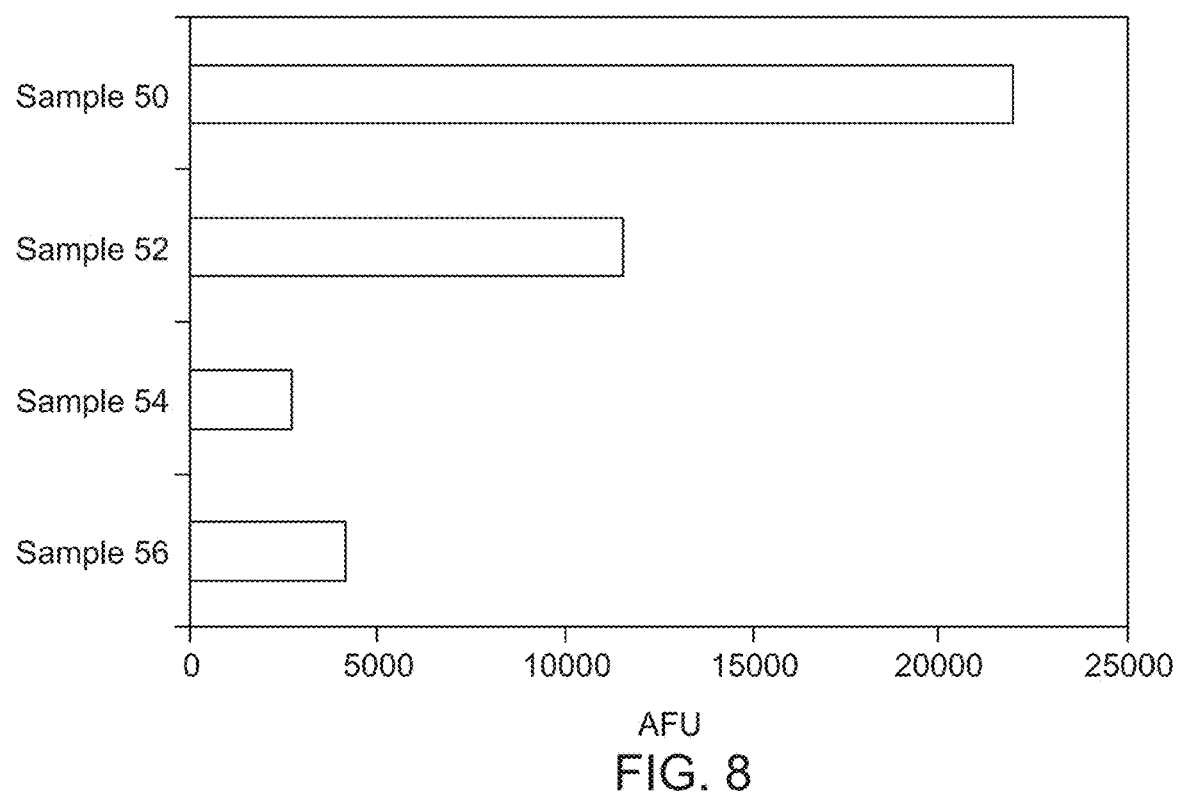
FIG. 8 illustrates the cell-free expression yield of IL-2 by image densitometry of FIG. 7.
Figure 9:
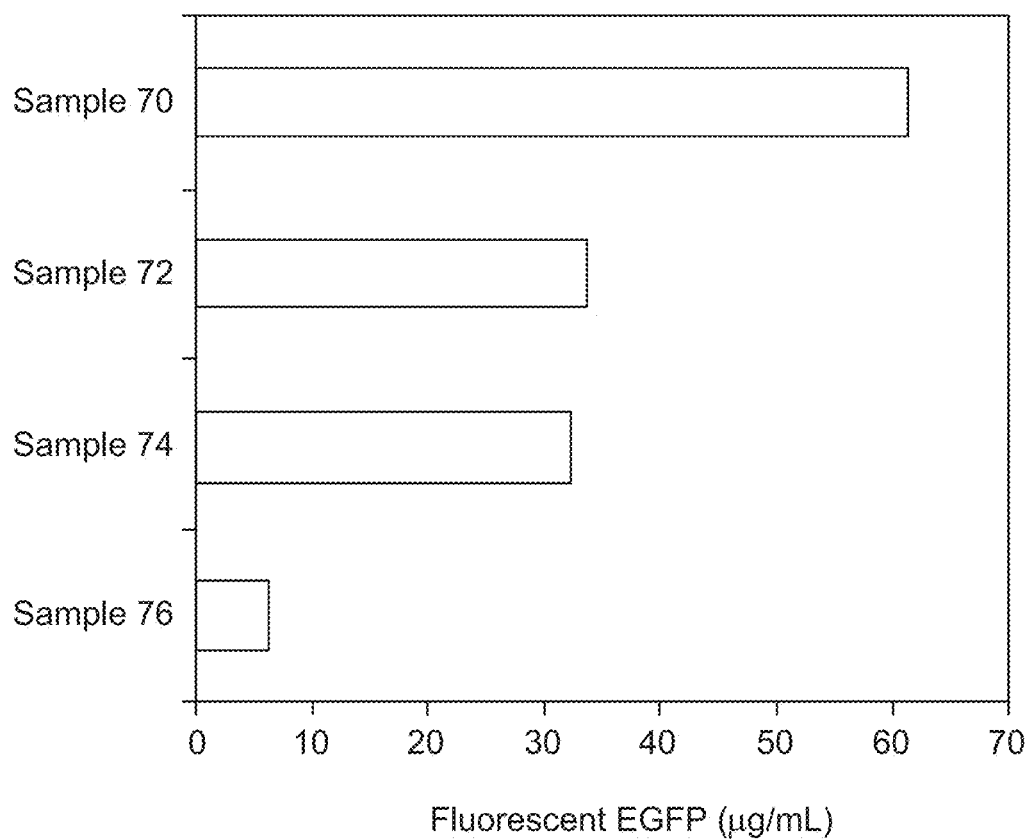
FIG. 9 illustrates enhanced expression of EGFP by in vitro transcription and translation of an RCA product that is generated from DNA mini-circles having minimalistic expression sequences in comparison with an RCA products derived from a plasmid DNA.

In one example, the expression of unexpected high-molecular weight proteins (26 kD-72 kD) was observed after codon-optimization of an RCA product 54 (derived from a DNA mini-circle of SEQ ID No. 8 encoding human IL-2, having a transcription termination sequence and codon-optimized for each individual codon) (FIG. 7). In the example provided in FIG. 7, the minimalistic IL2 expression sequences of the RCA product or PCR-amplified control DNA (derived from SEQ. ID. No. 7 and SEQ ID No. 8) were virtually identical except for codon usage within the IL-2 open reading frame. The SEQ ID No.8 was codon-optimized according to the JCat tool [Grote et al., Nucleic Acids Res. Jul. 1, 2005; 33 (Web Server issue: W 526-531). JCat: a novel tool to adapt codon usage of a target gene to its potential expression host.], which maximizes individual codon usage in a target gene to the codon preferences of an expression host. In contrast, SEQ ID No. 7 was contextually adapted based on a codon optimization process starting from the natural coding sequence of human IL-2, wherein only specific sites were re-coded. The coding sequence of IL-2 comprises two di-lysine repeats, which were re-coded into polyA tracts by the JCat tool because the AAA codon is significantly preferred over AAG in $E.$ $coli$. These di-lysine repeats were not substantially re-coded in SEQ ID No. 7 through the contextual codon optimization process. AAAAAA tracts are often known as ribosomal slippery sequences that can frameshift the translated product (Yan et al., Cell. 160:870-81, 2015) and exert additional translational control through ribosomal stalling (Arthur et al., Sci Adv. 1: e1500154, 2015). For linear DNA templates encoding IL2, such a frameshift may alter the translated product such that downstream translational stop codons are read-through. However, because the linear DNA template is finite, the corresponding mRNA transcript is also finite and the ribosome eventually reaches the end of the message (after frameshift) and stalls without releasing a translated product. In the example, an RCA product derived from a DNA mini-circle generated from SEQ ID No. 8, an RCA product which is a concatamer of tandem IL2 repeat sequences comprising AAAAAA ribosomal slippery sequences. When polycistronic run-off products are transcribed from the RCA product by read-through of transcription terminator sequences, then ribosomal slippery sequences in the corresponding polycistronic message contribute to additional read-through of translational stop codons. Consequently, the polycistronic message generates high-molecular weight translated products that are not IL-2 but rather off-target, high-molecular weight, and undesirable. In fact, transcriptional termination by RNA polymerases is highly inefficient due to various factors, including sequence-specific parameters and environmental parameters that affect RNA folding. Generally T7 RNA polymerase terminates with only 52% efficiency at Class I/II transcriptional termination sequences derived from the $E.$ $coli$ rrnB operon, and the efficiency of transcription termination declines as a function of increasing concentrations of dNTP. Thus the data presented in FIGS. 8 and 9 show that tandem repeats of cistronic or polycistronic mRNAs are widely generated from an RCA product template in coupled transcription-translation reactions (despite the presence of transcription termination sequences) and the corresponding mRNA may be effectively or ineffectively processed by ribosomes depending in part on codon usage, which ultimately enhances or reduces cell-free protein yield depending on whether the downstream cistrons in the message are designed appropriately.

Figure 3:
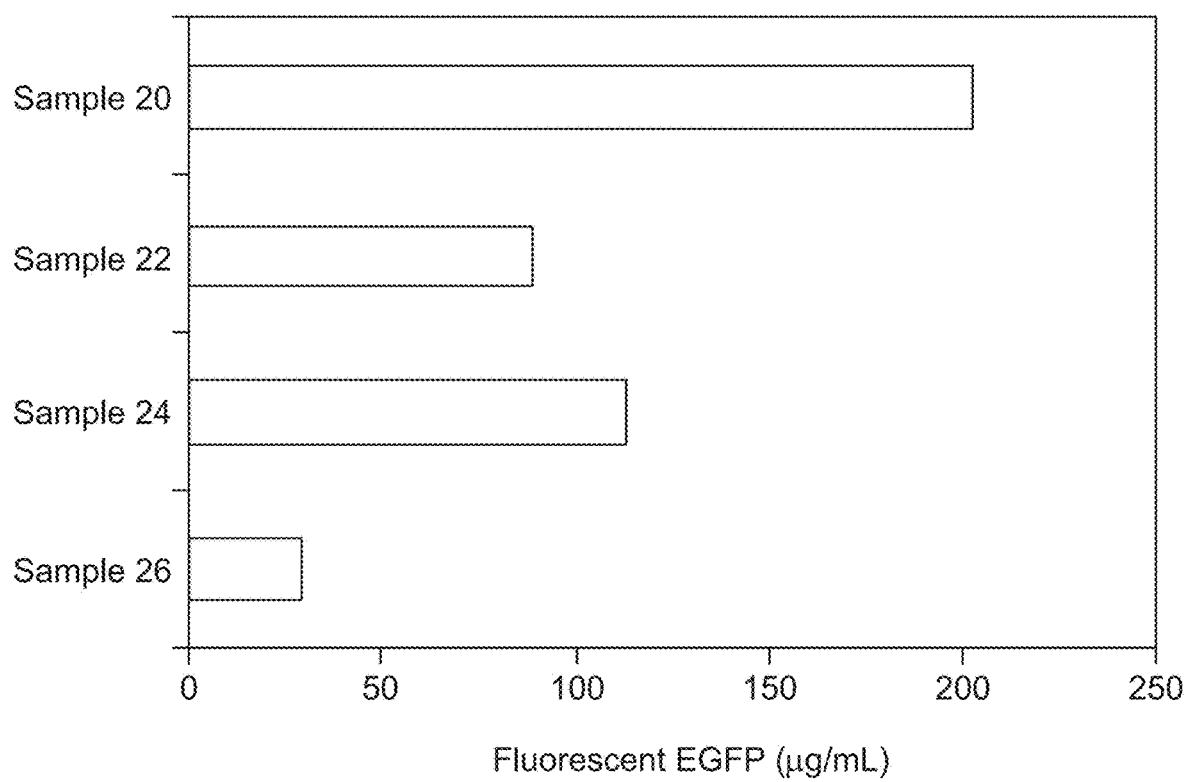
FIG. 3 illustrates the increased expression of an enhanced green fluorescent protein (EGFP) when an RCA product derived from a DNA mini-circle was used for in vitro transcription and translation as compared to PCR-amplified DNA templates, wherein the EGFP coding region was designed using contextual codon preference.
Figure 4:
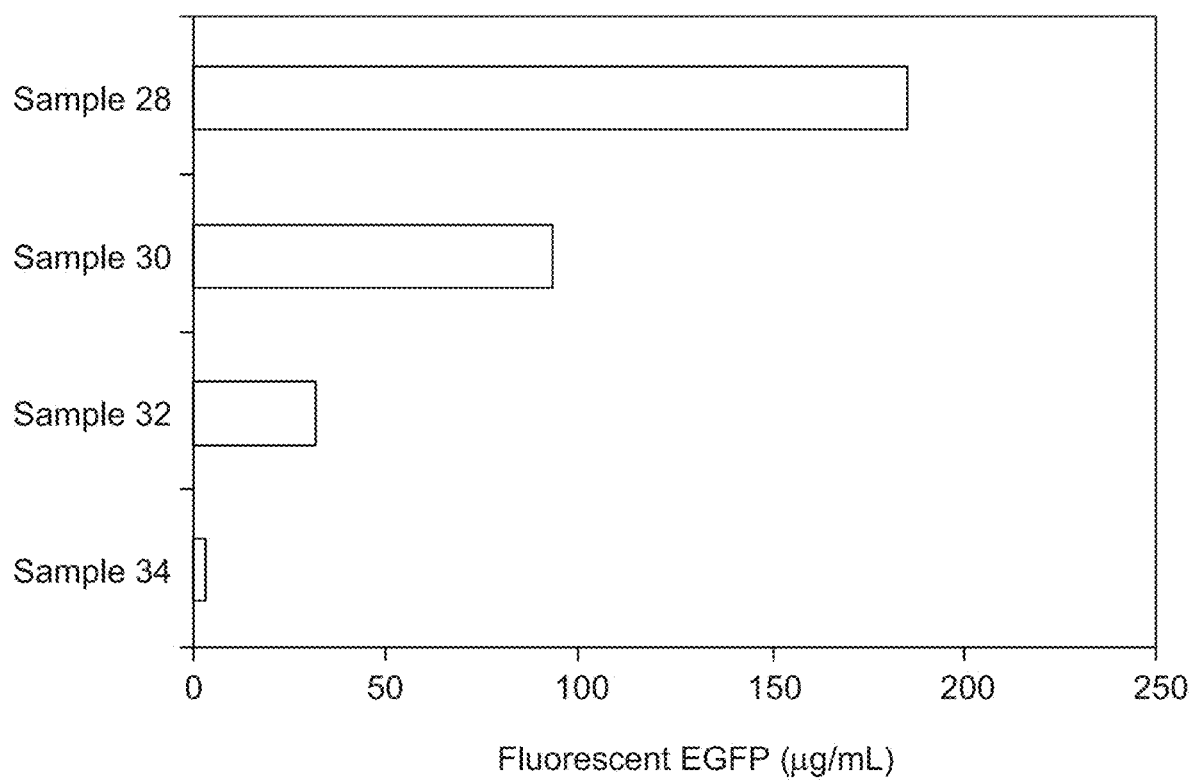
FIG. 4 illustrates the enhanced expression of EGFP when an RCA product derived from DNA mini-circle was used for in vitro transcription and translation as compared to PCR-amplified DNA templates, wherein the EGFP coding region was designed using individual codon preference.

In another example of codon optimization, SEQ ID No.2 and SEQ ID No.4 includes EGFP open reading frames that are codon-optimized according to the JCat tool, which maximizes individual codon usage of a target gene to the codon preferences of an expression host. Further, SEQ ID No. 1 and SEQ ID No.3 includes open reading frames for EGFP that are contextually adapted based on the following process; starting from the natural coding sequence of EGFP, only specific sites were re-coded to avoid cryptic start sites (ATG), cryptic ribosomal binding sites (for example, AGGA, GAGG, GGAG), class II termination sequences [(A, C, or T)ATCTGTT], ribosomal slippery sequences [NNNYYY, where Y(A, T)], and ribosomal pause sites (for example, AGG, GGA, GAG, GGG, GGT, GTG) upstream of internal ATG methionines. The data presented in FIGS. 3 and 4 illustrate that the cell-free expression yield of EGFP is partially influenced by codon usage.

In some embodiments, the open reading frame of the minimalistic expression sequence comprises a tag sequence for purification of the expressed protein. The tag sequence may be an affinity tag, tag for protease cleavage or combinations thereof. The affinity tag may be used for rapid purification and detection of recombinant proteins. The affinity tag may include a polyhistidine tag (his6 (SEQ ID NO: 9)), Glutathione S-transferase tag (GST), haemagglutinin (HA), myc (derived from c-myc gene product), FLAG (consisting of eight amino acids Asp-Tyr-Lys-Asp-Asp-Asp-Asp-Lys (SEQ ID NO: 10) including an enterokinase-cleavage site) or combinations thereof. Although fusion tags help in rapid purification or detection of the desired protein, the tags may not be considered to be permanent fixtures or domains of the recombinant proteins. Hence, removal of the fusion tag is often needed for highly analytical studies of recombinant protein structure and function. The tag for purification may be removed from the protein by using another type of tag, such as protease cleavage tag. The protease cleavage tag may be used to cleave a distinct peptide bond within a specific protein or peptide sequence. The protease cleavage tag may include, for example, Pre-Scission Protease tag (GE Healthcare) or thrombin protease tag (GE Healthcare).

As noted, in some embodiments, the minimalistic expression sequence further consists essentially of a transcription termination sequence. The transcription termination sequence is generally situated at the 3' end of a gene in a DNA template. Transcription termination sequences provide signals in the newly synthesized mRNA to initiate the process of releasing the mRNA from the transcriptional complex, which can also aid in effective translation of the desired protein product.

Figure 6:
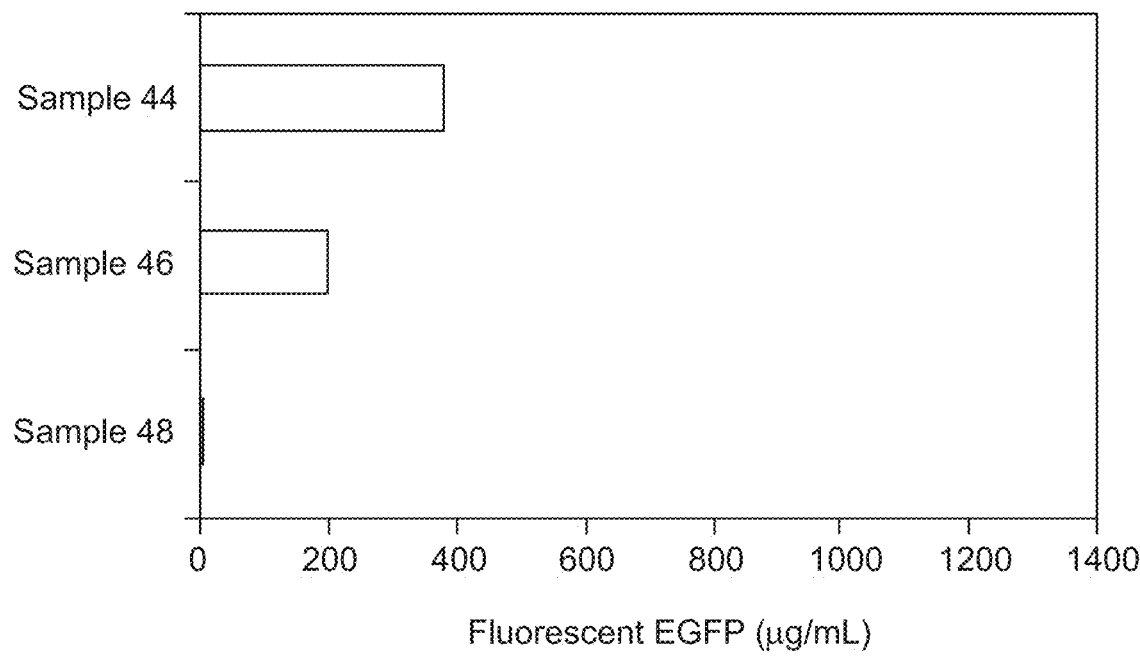
FIG. 6 illustrates yields of EGFP expression by in vitro transcription and translation using an RCA product derived from a DNA mini-circle, with or without thioated nucleotides, and a PCR-amplified DNA without any thioated nucleotides.

The effects of inefficient transcription termination in an RCA product derived from a mini-circle are largely inconsequential compared to an RCA product derived from a plasmid DNA. In some cases, plasmid DNA containing a gene of interest must be digested using a restriction enzyme to create a double-stranded DNA break immediately after the gene to prevent transcription from proceeding beyond that point when RCA product is derived from the plasmid. If run-off transcription were to occur, the other sections of the plasmid containing many coding and non-coding sequences (including sequences for the origin of replication, antibiotic selection, and accessory sequences that are used for selection, screening and/or propagation of the plasmid in a host cell) would be transcribed. RCA product derived from the plasmid DNA, when used in an undigested state, may produce unwanted mRNA species, via transcriptional readthrough, that risk production of protein contaminants together with (or in a greater amount than) the protein of interest. However, poor transcription termination in an RCA product derived from a mini-circle may still generate on-target mRNA. Consequently, the yield of cell-free protein is better from an RCA product derived from a DNA mini-circle compared to either an RCA product derived from a plasmid or PCR-amplified plasmid DNA. Similar expression benefits are observed even when the RCA product derived from a DNA mini-circle is completely devoid of transcription termination sequences, which is an unexpected result. This is illustrated in different examples, such as Examples 2 and 3, and the results are depicted in FIGS. 3, 4 and 6. For the examples provided in FIGS. 3 and 4, SEQ ID No.1 and SEQ ID No.2 encode EGFP with transcription termination sequences, whereas SEQ ID No.3 and SEQ ID No.4 encode EGFP without transcription termination sequences. An RCA product 22 (derived from DNA mini-circles of SEQ ID No.3) generated higher expression of EGFP compared to a PCR-amplified DNA product 26 (derived from SEQ ID No.3), and overall EGFP yield from RCA product 22 (derived from DNA mini-circles of SEQ ID No.3) was comparable to the PCR-amplified DNA product 24 (derived from SEQ ID No. 1) (FIG. 3). Using a different codon optimization strategy for EGFP, the RCA product 30 (derived from DNA mini-circles of SEQ ID No.4) generated higher amounts of EGFP than either the PCR-amplified DNA product 32 (derived from DNA of SEQ ID No. 2) or PCR-amplified DNA product 34 (derived from DNA of SEQ ID No.4) (FIG. 4). However, EGFP expression yield was maximal using RCA products 20 (derived from DNA mini-circles of SEQ ID No. 1) and 28 (derived from DNA mini-circles of SEQ ID No. 2). These examples show that transcriptional termination sequences, while essential for protein expression from PCR-amplified DNA, are not essential for robust protein expression from RCA products derived from DNA mini-circles. These RCA products improve cell-free protein expression by generating tandem repeats of cistronic mRNA species, wherein every cistron of the mRNA comprises the desired target gene. The tandem repeats of the cistron may in turn improve the mRNA stability, particularly when transcription termination signals are absent, and contribute to higher translational flux of the desired protein product.

In one or more embodiments, the method for in vitro transcription and translation employs a double-stranded RCA product as DNA template. In these embodiments, the intramolecular ligation of a double-stranded DNA template generates a double-stranded DNA mini-circle, which is employed as a template for the RCA reaction. The RNA polymerases used in cell-free transcription reactions (for example, T7 RNA polymerase) generally require double-stranded DNA promoter sequences for effective binding to DNA coding sequences. The effective binding of RNA polymerase to the double-stranded DNA promoter sequence initiates efficient transcription. Thus, RCA reaction conditions that promote the generation of double-stranded RCA products are desired for effective in vitro transcription and translation.

In some embodiments, the double-stranded RCA product is provided to the cell-free expression system without any further processing. In one embodiment, the RCA product is added to the cell-free system directly after amplification. The term "further processing" is meant to include an act of restriction digestion, ligation, or combinations thereof of the RCA product. However, in some embodiments, the RCA product may be separated (e.g., by precipitation) to remove salts or any other contaminants, such as primers or smaller fragmented DNA from the reaction medium before proceeding for cell-free expression using a eukaryotic cell-extract.

In one exemplary embodiment, the double-stranded RCA product has tandem repeats of a minimalistic expression sequence. In this embodiment, the minimalistic expression sequence is devoid of any extraneous sequences that are required for propagation of the DNA in a host cell. Further, the double-stranded RCA products of this embodiment are provided to the cell-free expression system without any restriction digestion and/or ligation.

Protein yields from cell-free expression reactions employing RCA products generated from DNA mini-circles are much higher than that of RCA products generated from plasmid DNA, which is described in detail in Example 5 and depicted in FIG. 9. In this example, cell-free yield of EGFP was enhanced when an RCA product 70 (derived from DNA mini-circles of SEQ ID No.1 encoding EGFP with a transcription termination sequence) was expressed compared to RCA product 72 (derived from plasmid comprising SEQ ID No.1). Further, in the absence of a transcription termination sequence, the expression of EGFP was also enhanced using an RCA product 74 (derived from DNA mini-circles of SEQ ID No.3) relative to RCA product 76 (derived from plasmid DNA comprising SEQ ID No.3). These examples show that the presence of extraneous sequences (such as origin of replication, antibiotic selection and lacZ selection sequences) repeated as concatemers within the RCA product of plasmid DNA hinder cell-free expression of the desired protein target.

Cell-free expression of RCA products derived from DNA mini-circles also results in higher protein yield compared to nucleic acids amplified by PCR. For example, synthesis of EGFP protein by coupled in vitro transcription and translation were compared between PCR-amplified DNA and RCA products derived from DNA mini-circles. The enhanced yield of EGFP when RCA products 20, 22 and 28, 30 were expressed compared to using PCR-amplified DNA 24, 26 and 32, 34, respectively, are shown in FIGS. 3 and 4.

Figure 5:
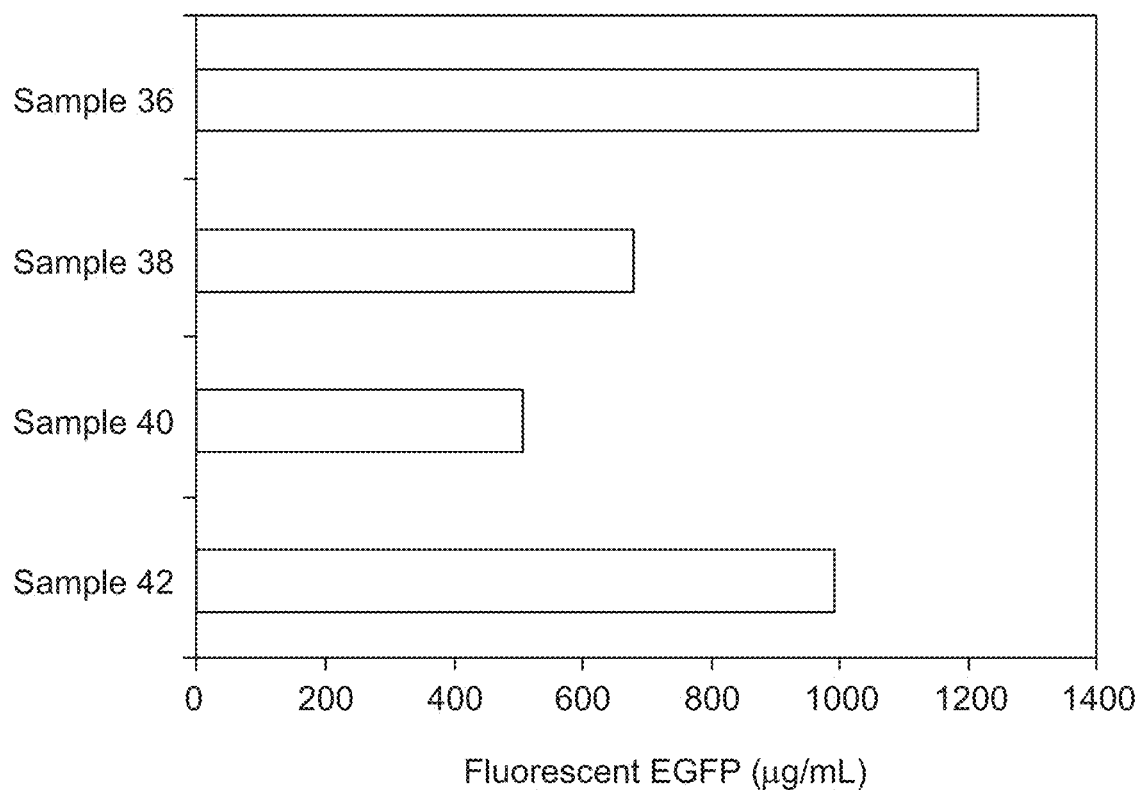
FIG. 5 illustrates yields of EGFP expression by in vitro transcription and translation using an RCA product derived from a DNA mini-circle, with or without thioated nucleotides, and a PCR-amplified DNA without any thioated nucleotides.

In some embodiments, the double-stranded RCA product that is used for in vitro transcription-translation reaction comprises thioated nucleotides. In these embodiments, the RCA reactions are supplemented with thioated dNTPs, such as $\alpha$-S-dATP or $\alpha$-S-dTTP, into the dNTP mixture for random incorporation of thioated bases into the RCA DNA product while amplification. Cell-free protein expression is improved when an RCA product comprising thioated nucleotides is used for in vitro transcription and translation when compared to non-thioated RCA products. For example, EGFP protein yield was higher when thioated RCA product 36 (derived from a DNA mini-circle of SEQ ID No.5) was expressed relative to either PCR-amplified DNA product 42 (derived from DNA of SEQ ID No.5) or non-thioated RCA product 38 (derived from a DNA mini-circle of SEQ ID No.5 with AT hexamers) or non-thioated RCA product 40 (derived from a DNA mini-circle of SEQ ID No.5 with random hexamer), as shown in FIG. 5. Further, in another example wherein transcription termination sequences were removed downstream of the EGFP coding sequence, cell-free EGFP protein yield was much higher when thioated RCA product 44 (derived from DNA mini-circles of SEQ ID No.6) was expressed compared to either non-thioated PCR-amplified DNA product 48 (derived from DNA of SEQ ID No.6) or non-thioated RCA product 46

(derived from a DNA mini-circle of SEQ ID No.6 with AT hexamer), as shown in FIG. 6.

The present method for cell-free protein expression includes in vitro transcription and in vitro translation. The in vitro transcription reaction employs double-stranded RCA product, wherein the double-stranded RCA product consists essentially of tandem repeats of a minimalistic expression sequence. The minimalistic expression sequence includes a promoter sequence. The promoter sequence is present upstream (5') of the gene of interest to be transcribed. DNA-dependent RNA polymerases bind to the double-stranded DNA promoter region to initiate gene transcription. A variety of suitable RNA polymerases is known in the art and includes those having only one subunit (for example, those from bacteriophages like T3 and T7, and mitochondria) as well as multi-domain RNA polymerases derived from bacteria and eukaryotes. The RNA polymerase may further require additional protein co-factors for efficient transcription.

In some embodiments of the cell-free translation reaction, a biomolecular translational machinery is extracted from cells and utilized for in vitro translation. In one or more embodiments, the codon optimized sequence of the open reading frame enhances the rate of translation. The composition, proportion of enzymes, and building blocks required for translation are provided by the cell-free extract or may be supplemented with synthetic components. The mRNAs synthesized by transcription are expressed in a translation reaction, which produces the target protein in the cell-free extract. In some embodiments of the in vitro expression reaction, protein synthesis occurs in cell-free extract rather than within cultured cells (The extracted material from cells may be referred to herein as a "cell-free extract" or "cell extract"). The cell extract contains generally the cytosolic and organelle components of the cell. The cell-free extract may supply all or most of the molecules required for cell-free transcription and translation, such as ribosomes for translation, tRNA and amino acids, enzymatic cofactors and an energy source, and cellular components essential for protein folding.

In some embodiments, the cell-free expression system comprises a prokaryotic cell extract, a eukaryotic cell extract, or a combination thereof. In yet another embodiment, the cell-free expression system is formulated from individually-purified components. In one embodiment, the cell extract developed for cell-free protein expression is derived from prokaryotic organisms. In this embodiment, the mRNA derived from RCA product DNA may be added to, or produced within, the prokaryotic extract to express a protein. The prokaryotic extracts capable of supporting translation may be derived from *E. coli*. In some other embodiments, the cell extract is derived from eukaryotic cells, such as protozoans, yeast cells, insect cells, mammalian cells, or human cells. In these embodiments, the mRNA derived from RCA product DNA may be added to, or produced within, the eukaryotic cell extract, such as, rabbit reticulocyte lysates (RRL), wheat germ extracts, insect cell lysates (such as SF9 or SF21), mammalian lysates (such as CHO), human lysates (such as HeLa), or protozoan lysate (such as *Leishmania*). The cell-free extracts derived from eukaryotic systems contain the necessary cellular macromolecules, such as ribosomes, translation factors and tRNAs required for efficient protein synthesis, wherein energy sources and amino acids may need to be supplemented.

In one exemplary embodiment, the nucleic acid template for RCA reaction is a deoxyribonucleic acid (DNA) template. The DNA template may be a synthetic DNA or a natural DNA. The DNA template may be a circular DNA template, a linear DNA template, or a nicked DNA template. In some embodiments, the nucleic acid template is a DNA mini-circle template, and RCA is used to amplify the DNA mini-circle template in a cell-free system. In one example embodiment, the circularization of the linear nucleic acid template is accomplished by an enzymatic reaction, for example, by incubation with a ligation enzyme such as DNA ligase. In some embodiments, the DNA mini-circle template includes a minimalistic expression sequence. In some embodiments, the RCA of the DNA mini-circle template contains a minimalistic expression sequence to produce a tandem repeat DNA sequence. The produced tandem repeat sequence consists essentially of multiple units of the minimalistic expression sequence. The RCA product used for in vitro transcription-translation may be in an intact, non-degraded state.

The rolling-circle amplification reaction often employs reagents such as a primer, a polymerase, and free nucleotides (dNTPs). In some embodiments. RCA may be performed by contacting a double-stranded DNA mini-circle with a primer solution comprising a random primer mixture to form a nucleic acid template-primer complex; contacting the nucleic acid template-primer complex with a DNA polymerase and deoxyribonucleoside triphosphates; and amplifying the nucleic acid template. The nucleic acid polymerase that is employed in the amplification reaction may be a proofreading nucleic acid polymerase. RCA may be performed by using any of the DNA polymerases that are known in the art, including, but not limited to, a Phi29 DNA polymerase. The amplification reaction mixture may further include additional reagents such as suitable amplification reaction buffers.

In some embodiments, each of the reagents used in the nucleic acid amplification reaction may be pre-treated to remove any contaminating nucleic acids. In some embodiments, the pre-treatment of the reagents includes incubating the reagents in presence of ultraviolet radiation. In some other embodiments, the reagents are de-contaminated by incubating the reagents in presence of a nuclease and its co-factor (for example, a metal ion). Suitable nucleases include, but are not limited to, exonucleases such as exonuclease I or exonuclease III. In some embodiments, the proofreading DNA polymerases used for DNA amplification reaction may be de-contaminated by incubating with a divalent metal ion (for example, magnesium or manganese ions) in absence of dNTPs.

The RCA reaction may be performed using a random primer mixture. In some embodiments, specific primers are used for the RCA reaction. Primer sequences comprising one or more nucleotide analogues may also be used. In one or more embodiments, the RCA is performed using a random primer mixture comprising a nucleotide analogue. The nucleotide analogue may be an inosine, a Locked Nucleic Acid (LNA) nucleotide, a Peptide Nucleic Acid (PNA) nucleotide, a thioated nucleotide, 2-amino-deoxyadenosine, 2-thio-deoxythymidine, a polycation nucleotide, Zip Nucleic Acid (ZNA) polycation modified nucleotide, or combinations thereof. In one or more embodiments, the random primer mixture has a sequence +N+N(atN)(atN)(atN)*N (AT hexamer Primer). In some embodiments, nuclease-resistant primers (e.g., primer sequences comprising phosphorothioate groups at appropriate positions) are employed for the amplification reactions (e.g., NNNN*N*N). In some embodiments, the amplification of the DNA mini-circles employs random hexamers or a hexamer primer, +N+N(at N)(at N)(at N)*N (AT hexamer primer), where "N" represents a random nucleotide (i.e., N may be any of A, C, G, or T/U), "at N" represents a random mixture containing 2-amino dA, 2-thio-dT, normal G and normal C, a plus (+) sign preceding a letter designation denotes that the nucleotide designated by the letter is a locked nucleic acid (LNA) nucleotide, a star (*) sign preceding a letter denotes that the nucleotide designated by the letter is a phosphorothioate modified nucleotide.

During the amplification reaction, the DNA mini-circle template is replicated by a polymerase in the presence of deoxyribonucleoside triphosphates (dNTPs) or their modified counterparts. The free nucleotides employed in nucleic acid template amplification may include natural nucleotides (for example, dATP, dGTP, dCTP or dTTP) or their modified analogues. In some embodiments, the reaction mixture is supplemented with thioated dNTPs. The thioated dNTPs may include but are not limited to $\alpha$-S-dGTP, $\alpha$-S-dCTP, $\alpha$-S-dATP, and $\alpha$-S-dTTP. The thioated dNTPs such as $\alpha$-S-dATP or $\alpha$-S-dTTP may be added into the dNTP mixture for random incorporation of the thioated bases into the RCA product.

In some embodiments, the RCA is performed using a final concentration of dNTPs in a range of about 10 µM to about 10 mM. In one or more embodiments of RCA reactions, the dNTP concentration is less than 10 mM. In these embodiments, the concentration of dNTPs is kept lower than 10 mM to avoid hydrogel formation from the RCA product and to remain at a concentration below or equal to the amount of divalent cation (e.g. magnesium) present in the reaction buffer. Hydrogel formation may occur after amplification in the presence of a high concentration of dNTPs which may further complicate the downstream manipulation such as pipetting and processing of the RCA product. Hydrogel formation may be observed when dNTP concentration of 50 mM or more is used in the RCA reaction.

RCA may be performed using commercially available RCA amplification kits such as Illustra™ TempliPhi™ Amplification Kit (GE Healthcare). TempliPhi rolling-circle amplification employs modified random primers, which provide higher sensitivity and amplification balance. In some embodiments, nuclease-resistant primers are used for RCA reaction. Since high concentration of template DNA is required for the present method of in vitro transcription and translation, a more balanced DNA amplification with faster kinetics and higher yield may be achieved using RCA.

A variety of methods may be used to prepare a DNA mini-circle template for use with methods of the invention. In some embodiments, a linear DNA template may be circularized to generate a DNA mini-circle template. In one example embodiment, the circularization of the linear DNA template may be effected by an enzymatic reaction, for example, by incubation with a ligation enzyme such as DNA ligase. In some embodiments, the terminal ends of the linear DNA template are hybridized to a nucleic acid sequence such that the terminal ends come in close proximity. Incubating with a ligation enzyme may then effect the circularization of the hybridized linear DNA template to generate a DNA mini-circle. Suitable DNA mini-circle template may also be generated by PCR amplification of a portion of a larger DNA (for example, a genomic DNA, or a DNA from a DNA library) using appropriate PCR primers, followed by circularization of the PCR product. DNA mini-circle may also be generated by chemical synthesis of suitable linear oligonucleotides followed by circularization of the synthesized oligonucleotide. In some embodiments, the synthesized linear oligonucleotides may consist essentially of minimalistic expression sequence and achieve circularization via DNA ligase to generate DNA mini-circle.

One or more of the methods may further comprise steps of purifying, analyzing and/or quantifying the DNA mini-circles. Isolation or purification of the dsDNA mini-circles and/or removal of the contaminants, such as enzymes or non-ligated form of DNA may be performed prior to the amplification reaction. Any suitable techniques that are used for purification, analysis or quantification of nucleic acids may be employed. Non-limiting examples include precipitation, filtration, affinity capture, gel electrophoresis, sequencing or HPLC analysis. For example, the purification of the circular nucleic acids may be achieved by affinity capture. In some embodiments, the methods may further comprise processing of the generated DNA mini-circle. Post-processing of the generated DNA mini-circle may vary according to the intended use.

EXAMPLES

Unless specified otherwise, ingredients described in the examples are commercially available from common chemical suppliers. Some abbreviations used in the examples section are expanded as follows: "mg": milligrams; "ng": nanograms; "pg": picograms; "fg": femtograms: "mL": milliliters: "mg/mL": milligrams per milliliter; "mM": millimolar: "mmol": millimoles; "pM": picomolar; "pmol": picomoles; "µL": microliters: "min.": minutes and "h.": hours.

FIG. 1 is a schematic representation of one of the general embodiments of the methods of in vitro transcription and translation using an RCA product derived from a DNA mini-circle. A DNA expression construct 10 that consists essentially of a minimalistic expression sequence 12 is circularized by a ligation reaction to generate a DNA mini-circle 14. The DNA mini-circle 14 is amplified by RCA. The amplification reaction generates a concatamer RCA product 16 having tandem repeat units of the expression construct 10, containing the minimalistic expression sequence 12, which is devoid of any extraneous sequences. As such, the DNA mini-circle is not amenable to propagation inside a cell. The RCA product 16 is then expressed in an in vitro transcription-translation reaction. In some examples, the minimalistic expression sequence of the DNA mini-circle 14 contains a transcription termination sequence. The RCA product formed from such a DNA mini-circle will have a transcription termination sequence in each of the tandem repeats. Subsequently, the mRNA 17 produced from the RCA product 16 of this example may be terminated at the transcription termination sequence at each tandem repeat units. However, if read-through of any one of the transcription termination sequences occurs (such as the mRNA 18), the downstream mRNA sequence still encodes for the anticipated protein target. In some other examples, the minimalistic expression sequence of the DNA expression construct 10 does not contain a transcription termination sequence. The mRNA 18 produced from the RCA product of such examples does not get terminated at each tandem repeat unit, and thus transcribes continuously through multiple tandem repeat sequences of the RCA product. However, in either case, the mRNA is translated into a protein with a desired sequence 19 due to the presence of translational termination sequences in the DNA expression construct 10.

Example 1: Rolling Circle Amplification of DNA Mini-Circle

Generation of DNA Mini-Circle:

A minimalistic expression sequence for EGFP and human interleukin-2 (IL-2) were designed in silico and synthesized in vitro. All of these expression sequences contained a T7 promoter and +1 sequence (first ribobase position of the 5' untranslated region of the resulting mRNA) followed by a T7 phi10 promoter stem-loop sequence. A variety of additional non-coding and coding parameters were included during the designing of the minimalistic expression sequence, including; T7 pre-promoter sequences, ribosomal binding sequences, insulator sequences for enhancing ribosomal binding, insulator sequences for enhancing ribosomal initiation, transcription termination sequences, translational start and stop sequences, leader-sequence protease cleavage sites, and codon optimization. Representative minimalistic expression sequences with these parameters are listed as SEQ ID No. 1-8 (Table 2). The sequences range in size from 655-970 base pairs.

TABLE 2

Sequences of various minimalistic expression sequences.

| SEQ ID No. | Sequences |
| --- | --- |
| 1 | CCGGAATTCGGATCCGAAATTAATACGACTCACTATAGGG AGACCACAACGGTTTCCCTCTAGCGTAAGGAGGTTTGGAA TGCATCACCATCACCATCACGGCTCACTGGAAGTTCTGTTC CAGGGGCCCGGCTCAGTAAGCAAGGGCGAAGAGCTGTTCA CCGGGGTTGTGCCCATCCTGGTCGAGCTGGACGGCGACGT AAACGGCCACAAGTTCAGCGTGTCCGGCGAAGGCGAAGGC GACGCCACCTACGGCAAGCTGACCCTGAAGTTCATCTGCA CCACCGGCAAGCTGCCCGTGCCCTGGCCCACCCTCGTGACC ACCCTGACCTACGGCGTGCAGTGCTTCAGCCGCTACCCCGA CCACATGAAGCAGCACGACTTCTTCAAATCCGCCATGCCCG AAGGCTACGTCCAAGAGCGCACCATCTTCTTCAAAGACGA CGGCAACTACAAGACCCGCGCCGAAGTGTGTTCGAAGGC GACACCCTGGTGAACCGCATCGAGCTGAAGGGCATCGACT TCAAAGAAGACGGCAACATCCTGGGGCACAAGCTCGAGTA CAACTACAACAGCCACAACGTCTATATCATGGCCGACAAG CAGAAGAACGGCATCAAGGTGAACTTCAAGATCCGCCACA ACATCGAAGACGGCAGCGTGCAGCTCGCCGACCACTACCA GCAGAACACCCCCATCGGCGACGGCCCCGTGCTGCTGCCC GACAACCACTACCTGAGCACCCAGTCCGCCCTGAGCAAAG ACCCCAACGAAAAGCGCGATCACATGGTCCTGCTCGAGTT CGTGACCGCCGCCGGCATCACTCTCGGCATGGACGAGCTG TACAAGTAATAATACTAGAGCCAGGCATCAAATAAAACGA AAGGCTCAGTCGAAAGACTGGGCCTTTCGTTTTATCTGTTG TTTGTCGGTGAACGCTCTCTACTAGAGCGCGGATCCGGTAC CCCG |
| 2 | CCGGAATTCGGATCCGAAATTAATACGACTCACTATAGGG AGACCACAACGGTTTCCCTCTAGCGTAAGGAGGTTTGGAA TGCATCATCACCATCACCACGGCTCACTGGAAGTTCTGTTC CAGGGGCCCGGCTCAGTTTCTAAAGGTGAAGAACTGTTCA CCGGTGTTGTTCCGATCCTGGTTGAACTGGACGGTGACGTT AACGGTCACAAATTCTCTGTTTCTGGTGAAGGTGAAGGTGA CGCTACCTACGGTAAACTGACCCTGAAATTCATCTGCACCA CCGGTAAACTGCCGGTTCCGTGGCCGACCCTGGTTACCACC CTGACCTACGGTGTTCAGTGCTTCTCTCGTTACCCGGACCA CATGAAACAGCACGACTTCTTCAAATCTGCTATGCCGGAA GGTTACGTTCAGGAACGTACCATCTTCTTCAAAGACGACGG TAACTACAAAACCCGTGCTGAAGTTAAATTCGAAGGTGAC ACCCTGGTTAACCGTATCGAACTGAAAGGTATCGACTTCAA AGAAGACGGTAACATCCTGGGTCACAAACTGGAATACAAC TACAACTCTCACAACGTTTACATCATGGCTGACAAACAGA AAAACGGTATCAAAGTTAACTTCAAAATCCGTCACAACAT CGAAGACGGTTCTGTTCAGCTGGCTGACCACTACCAGCAG AACACCCCGATCGGTGACGGTCCGGTTCTGCTGCCGGACA ACCACTACCTGTCTACCCAGTCTGCTCTGTCTAAAGACCCG AACGAAAAACGTGACCACATGGTTCTGCTGGAATTTGTTAC |

TABLE 2-continued

Sequences of various minimalistic expression sequences.

| SEQ ID No. | Sequences |
| --- | --- |
| | CGCTGCTGGTATCACCCTGGGTATGGACGAACTGTACAAAT AATAATACTAGAGCCAGGCATCAAATAAAACGAAAGGCTC AGTCGAAAGACTGGGCCTTTCGTTTTATCTGTTGTTTGTCG GTGAACGCTCTCTACTAGAGCGCGGATCCGGTACCCCG |
| 3 | CCGGAATTCGGATCCGAAATTAATACGACTCACTATAGGG AGACCACAACGGTTTCCCTCTAGCGTAAGGAGGTTTGGAA TGCATCACCATCACCATCACGGCTCACTGGAAGTTCTGTTC CAGGGGCCCGGCTCAGTAAGCAAGGGCGAAGAGCTGTTCA CCGGGGTTGTGCCCATCCTGGTCGAGCTGGACGGCGACGT AAACGGCCACAAGTTCAGCGTGTCCGGCGAAGGCGAAGGC GACGCCACCTACGGCAAGCTGACCCTGAAGTTCATCTGCA CCACCGGCAAGCTGCCCGTGCCCTGGCCCACCCTCGTGACC ACCCTGACCTACGGCGTGCAGTGCTTCAGCCGCTACCCCGA CCACATGAAGCAGCACGACTTCTTCAAATCCGCCATGCCCG AAGGCTACGTCCAAGAGCGCACCATCTTCTTCAAAGACGA CGGCAACTACAAGACCCGCGCCGAAGTGAAGTTCGAAGGC GACACCCTGGTGAACCGCATCGAGCTGAAGGGCATCGACT TCAAAGAAGACGGCAACATCCTGGGGCACAAGCTCGAGTA CAACTACAACAGCCACAACGTCTATATCATGGCCGACAAG CAGAAGAACGGCATCAAGGTGAACTTCAAGATCCGCCACA ACATCGAAGACGGCAGCGTGCAGCTCGCCGACCACTACCA GCAGAACACCCCCATCGGCGACGGCCCCGTGCTGCTGCCC GACAACCACTACCTGAGCACCCAGTCCGCCCTGAGCAAAG ACCCCAACGAAAAGCGCGATCACATGGTCCTGCTCGAGTT CGTGACCGCCGCCGGCATCACTCTCGGCATGGACGAGCTG TACAAGTAATAATACTAGAGCGCGGATCCGGTACCCCG |
| 4 | CCGGAATTCGGATCCGAAATTAATACGACTCACTATAGGG AGACCACAACGGTTTCCCTCTAGCGTAAGGAGGTTTGGAA TGCATCATCACCATCACCACGGCTCACTGGAAGTTCTGTTC CAGGGGCCCGGCTCAGTTTCTAAAGGTGAAGAACTGTTCA CCGGTGTTGTTCCGATCCTGGTTGAACTGGACGGTGACGTT AACGGTCACAAATTCTCTGTTTCTGGTGAAGGTGAAGGTGA CGCTACCTACGGTAAACTGACCCTGAAATTCATCTGCACCA CCGGTAAACTGCCGGTTCCGTGGCCGACCCTGGTTACCACC CTGACCTACGGTGTTCAGTGCTTCTCTCGTTACCCGGACCA CATGAAACAGCACGACTTCTTCAAATCTGCTATGCCGGAA GGTTACGTTCAGGAACGTACCATCTTCTTCAAAGACGACGG TAACTACAAAACCCGTGCTGAAGTTAAATTCGAAGGTGAC ACCCTGGTTAACCGTATCGAACTGAAAGGTATCGACTTCAA AGAAGACGGTAACATCCTGGGTACAAACTGGAATACAAC TACAACTCTCACAACGTTTACATCATGGCTGACAAACAGA AAAACGGTATCAAAGTTAACTTCAAAATCCGTCACAACAT CGAAGACGGTTCTGTTCAGCTGGCTGACCACTACCAGCAG AACACCCCGATCGGTGACGGTCCGGTTCTGCTGCCGGACA ACCACTACCTGTCTACCCAGTCTGCTCTGTCTAAAGACCCG AACGAAAAACGTGACCACATGGTTCTGCTGGAATTTGTTAC CGCTGCTGGTATCACCCTGGGTATGGACGAACTGTACAAAT AATAATACTAGAGCGCGGATCCGGTACCCCG |
| 5 | CCGGGATCCTTCTTTAAATTAATACGACTCACTATAGGGAG ACCACAACGGTTTCCCTCTAGAAATAATTTTGTTTAACTTT AAGAAGGAGNTATACATATGCATCACCATCACCATCACGG CTCACTGGAAGTTCTGTTCCAGGGGCCCGGCTCAGTAAGCA AGGGCGAAGAGTTGTTACCCGGGGTTGTGCCGATCCTTGTC GAGCTTGACGGCGACGTAAACGGCCACAAGTTTAGCGTGT CCGGCGAAGGCGAAGGCGACGCAACGTACGGCAAGCTTAC GCTTAAGTTTATCTGCACGACGGGCAAGCTTCCGGTGCCGT GGCCGACGCTTGTGACGACGCTTACGTACGGCGTGCAGTG CTTTAGCCGCTACCCAGATCACATGAAGCAACACGATTTCT TTAAGTCCGCAATGCCCGAAGGCTACGTCCAAGAGCGCAC GATCTTCTTCAAAGACGACGGCAACTACAAGACGCGCGCA GAAGTGAAGTTTGAAGGCGATACGCTTGTGAACCGCATCG AGCTTAAGGGCATCGATTTCAAAGAAGACGGCAACATCCT TGGGCACAAGCTTGAGTACAACTACAACAGCCACAACGTC TATATCATGGCAGATAAGCAAAAGAACGGCATCAAGGTGA ACTTTAAGATCCGCCACAACATCGAAGACGGCAGCGTGCA ACTTGcAGATCACTACCAACAAAACACGCCGATCGGCGAC GGCCCGGTGCTTCTTCCGGATAACCACTACCTTAGCACGCA ATCCGCACTTAGCAAAGATCCGAACGAAAAGCGCGATCAC ATGGTCCTTCTTGAGTTTGTGACGGCAGCCGGCATCACGCT |

TABLE 2 -continued

Sequences of various minimalistic expression sequences.

| SEQ ID No. | Sequences |
|---|---|
|  | TGGCATGGACGAGCTTTACAAGTAATAACTAGCATAACCC CTTGGGGCCTCTAAACGGGTCTTGAGGGGTTTTTTGCTGCA GAGATCTCCG |
| 6 | CCGGGATCCTTCTTTAAATTAATACGACTCACTATAGGGAG ACCACAACGGTTTCCCTCTAGAAATAATTTTGTTTAACTTT AAGAAGGAGATATACATATGCATCACCATCACCATCACGG CTCACTGGAAGTTCTGTTCCAGGGGCCCGGCTCAGTAAGCA AGGGCGAAGAGTTGTTTACCGGGGTTGTGCCGATCCTTGTC GAGCTTGACGGCGACGTAAACGGCCACAAGTTTAGCGTGT CCGGCGAAGGCGAAGGCGACGCAACGTACGGCAAGCTTAC GCTTAAGTTTATCTGCACGACGGGCAAGCTTCCGGTGCCGT GGCCGACGCTTGTGACGACGCTTACGTACGGCGTGCAGTG CTTTAGCCGCTACCCAGATCACATGAAGCAACACGATTTCT TTAAGTCCGCAATGCCCGAAGGCTACGTCCAAGAGCGCAC GATCTTCTTCAAAGACGACGGCAACTACAAGACGCGCGCA GAAGTGAAGTTTGAAGGCGATACGCTTGTGAACCGCATCG AGCTTAAGGGCATCGATTTCAAAGAAGACGGCAACATCCT TGGGCACAAGCTTGAGTACAACTACAACAGCCACAACGTC TATATCATGGCAGATAAGCAAAAGAACGGCATCAAGGTGA ACTTTAAGATCCGCCACAACATCGAAGACGGCAGCGTGCA ACTTGCAGATCACTACCAACAAAACACGCCGATCGGCGAC GGCCCGGTGCTTCTTCCGGATAACCACTACCTTAGCACGCA ATCCGCACTTAGCAAAGATCCGAACGAAAAGCGCGATCAC ATGGTCCTTCTTGAGTTTGTGACGGCAGCCGGCATCACGCT TGGCATGGACGAGCTTTACAAGTAATAACTGCAGAGATCT CCG |
| 7 | CCGGAATTCGGATCCGAAATTAATACGACTCACTATAGGG AGACCACAACGGTTTCCCTCTAGCGTAAGGAGGTTTGGAA TGCATCACCATCACCATCACGGCTCACTGGAAGTTCTGTTC CAGGGGCCCGGCTCAGCACCTACTTCAAGTTCTACAAAGA AAACACAGCTACAACTCGAGCATTTACTGCTCGATTTACAG ATGATTTTGAACGGCATTAATAATTACAAGAATCCTAAACT CACCCGCATGCTCACATTTAAGTTTTACATGCCCAAGAAGG CCACAGAACTGAAACATCTTCAGTGTCTAGAAGAAGAACT CAAACCTCTGGAAGAAGTGCTCAACTTAGCTCAAAGCAAA AACTTTCACTTAAGACCCAGGGACTTAATCAGCAATATCAA CGTAATAGTTCTCGAACTAAAAGGCTCTGAAACAACATTC ATGTGTGAATACGCTGACGAGACAGCAACCATTGTAGAAT TTCTGAACCGTTGGATTACCTTTTGTCAAAGCATCATCTCA ACACTGACTTAATAATACTAGAGCCAGGCATCAAATAAAA CGAAAGGCTCAGTCGAAAGACTGGGCCTTTCGTTTTATCTG TTGTTTGTCGGTGAACGCTCTCTACTAGAGCGCGGATCCGG TACCCCG |
| 8 | CCGGAATTCGGATCCGAAATTAATACGACTCACTATAGGG AGACCACAACGGTTTCCCTCTAGCGTAAGGAGGTTTGGAA TGCATCATCACCATCACCACGGCTCACTGGAAGTTCTGTTC CAGGGGCCCGGCTCAGCTCCGACCTCTTCTTCTACCAAAAA AACCCAGCTGCAGCTGGAACACCTGCTGCTGGACCTGCAG ATGATCCTGAACGGTATCAACAACTACAAAAACCCGAAAC TGACCCGTATGCTGACCTTCAAATTCTACATGCCGAAAAAA GCTACCGAACTGAAACACCTGCAGTGCCTGGAAGAAGAAC TGAAACCGCTGGAAGAAGTTCTGAACCTGGCTCAGTCTAA AAACTTCCACCTGCCTCCGCGTGACCTGATCTCTAACATCA ACGTTATCGTTCTGGAACTGAAAGGTTCTGAAACCACCTTC ATGTGCGAATACGCTGACGAAACCGCTACCATCGTTGAATT TCTGAACCGTTGGATCACCTTCTGCCAGTCTATCATCTCTA CCCTGACCTAATAATACTAGAGCCAGGCATCAAATAAAAC GAAAGGCTCAGTCGAAAGACTGGGCCTTTCGTTTTATCTGT TGTTTGTCGGTGAACGCTCTCTACTAGAGCGCGGATCCGGT ACCCCG |

Linear double-stranded DNA was synthesized (GenScript, Inc.) with unique restriction sites at both the 5' and 3' ends (BamHI and BglII, respectively). To create the DNA mini-circle, the dsDNA was digested with both endonucleases to produce complementary sticky overhangs. This digested DNA was ligated using T4 DNA ligase. Restriction digestion and ligation steps were carried out either sequentially (e.g., in different tubes) or simultaneously (e.g., in the same tube) using reaction mixtures containing 20 U BamH1, 10 U BglII, 400 U T4 ligase, 1 mM ATP, 100 μg/mL bovine serum albumin (BSA), 100 mM NaCl, 10 mM $MgCl_2$, 50 mM Tris-HCl, pH 7.5, and 10 mM dithiothreitol (DTT). All ligation products (DNA mini-circle) were subsequently treated with Exonuclease I and Exonuclease III to digest any remaining linear DNA fragments. The Exonucleases were heat inactivated by incubating the ligation products at 80° C. for 20 min. After heat-inactivation of the exonuclease, 5 μL (25 ng of DNA) of the completed ligation reaction was employed directly for isothermal RCA reactions using Phi29 DNA polymerase.

Amplification of the DNA Mini-Circle

The RCA of a DNA mini-circle template yields a high molecular weight, hyper-branched concatamer consisting essentially of tandem repeats of a minimalistic expression sequence. RCA reagents, including water, reaction buffer, primers, and phi29 enzyme were pre-cleaned prior to the addition of ligated template and dNTPs to minimize off-target amplification. In some embodiments, the primer-nucleotide solution (primer-nucleotide mix) containing an exonuclease-resistant primer and the nucleotides (dNTPs) was decontaminated by incubating the primer-nucleotide mix with a combination of exonuclease I, exonuclease III and a single stranded DNA binding protein (SSB protein). The enzyme mix containing a DNA polymerase was decontaminated by incubating with a divalent cation (e.g., $Mg^{2+}$) optionally in presence of an exonuclease (if the DNA polymerase used included a non-proof-reading DNA polymerase). The amplification of the DNA mini-circle was performed using such decontaminated enzyme mix and the primer-nucleotide mix. For example, the polymerase solution containing 200 ng of Phi29 DNA polymerase was incubated with 0.1 unit of exonuclease III in 5 μL of 50 mM HEPES buffer (pH=8.0) containing 15 mM KCl, 20 mM $MgCl_2$, 0.01% Tween-20 and 1 mM TCEP. The incubation was performed either at 30° C. for about 60 min. or at 4° C. for 12 h. The decontaminated Phi29 DNA polymerase solution was transferred to an ice-bath and then was used in the target RCA assay without prior inactivation of the exonuclease III.

The amplification of the DNA mini-circles was performed using random hexamers or hexamer primers having the sequence +N+N(at N)(at N)(at N)*N (AT hexamers), where "N" represents a random nucleotide (i.e., N may be any of A, C, G, or T/U), "at N" represents a random mixture containing 2-amino dA, 2-thio dT, normal G and normal C, a plus (+) sign preceding a letter designation denotes that the nucleotide designated by the letter is a locked nucleic acid (LNA) nucleotide, a star (*) sign preceding a letter denotes that the nucleotide designated by the letter is a phosphorothioate modified nucleotide. For all RCA reactions, the dNTP concentration was maintained below 1 mM (typically 400-800 μM) to avoid hydrogel formation of the amplified RCA product DNA, which can potentially complicate the downstream process of transcription and translation from the RCA product.

DNA amplification reactions were performed by incubating the de-contaminated primer-nucleotide mix and the de-contaminated enzyme mix at 30° C. for about 400 min. with the DNA mini-circle template. The amplification reaction mixture composed of 40 μM primer, 400 μM dNTPs (400 μM each of dATP, dCTP, dGTP, dTTP); 1 pg of DNA mini-circle, and 200 ng phi29 DNA polymerase. The reaction mixture was incubated in 50 mM HEPES buffer (pH=8.0) containing 15 mM KCl, 20 mM $MgCl_2$, 0.01% (v/v) Tween-20, 1 mM TCEP. At the end of the incubation, the Phi29 DNA polymerase in the reaction mixture was inactivated by heating the reaction mixture at 65° C. for 10 minutes.

Figure 2:
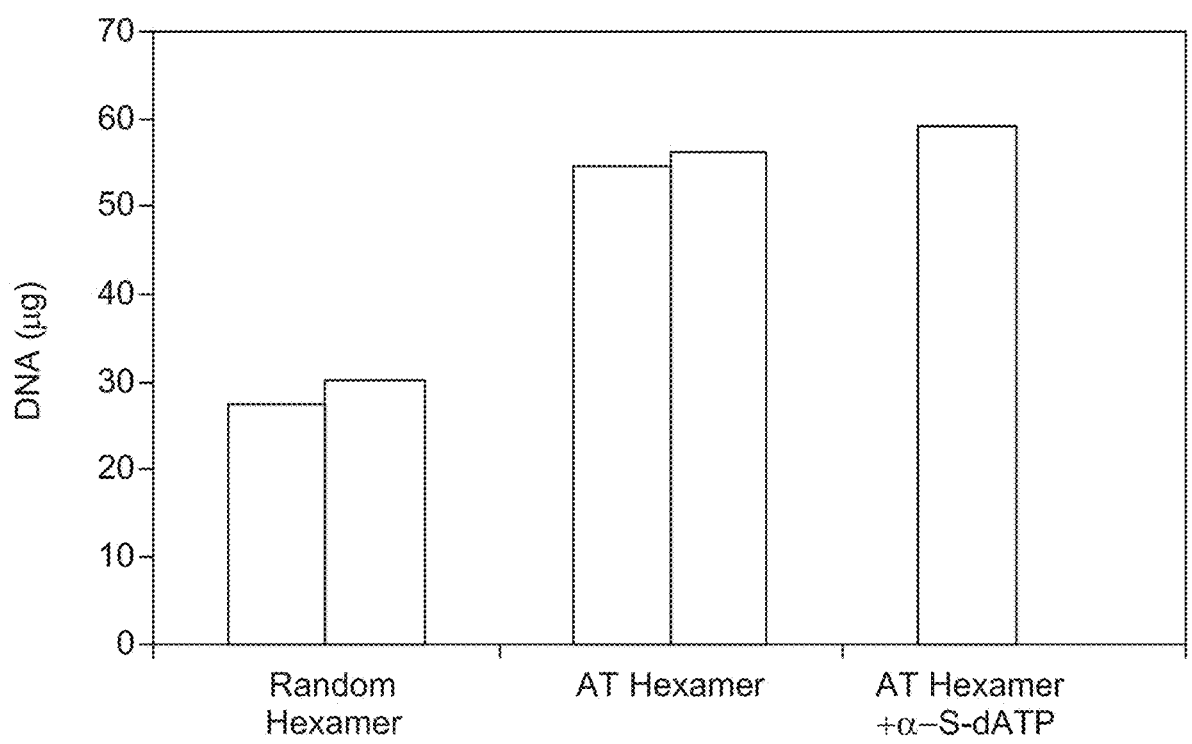
FIG. 2 illustrates the yield of an RCA product derived from DNA mini-circles using different primers and reaction conditions.

TABLE 3 and FIG. 2 summarize representative yields of the RCA products from the DNA mini-circle prepared using SEQ ID No. 6, which was digested with BamHI and BglII and circularized by ligation. RCA reactions were performed under three different test conditions, (i) using random hexamers and dNTPs. (ii) using AT-hexamer primers and dNTPs; and (iii) using AT hexamers and dNTPs mixed with thioated dATPs. RCA reactions were performed in duplicate (where possible) using approximately 28 ng of exonuclease-treated ligation product (DNA mini-circles). All RCA reactions comprised 0.4 mM dNTP and 40 µM of primer (either random hexamer or AT hexamer), except thioated dATP was added at a 1:40 ratio relative to non-thioated dATP for one reaction (0.01 mM alpha-S-dATP).

RCA products were quantified using Quant-It™ Picogreen® dsDNA Assay Kit (ThermoFisher Inc.) from a total RCA reaction volume of 100 µL. Agarose gel electrophoresis of the restricted DNA products was also performed, and the intensity of the electrophoresis bands was compared to those of standards having known concentration of DNA. The yield of RCA product DNA by using AT hexamers, random hexamers, and AT hexamers and dNTPs mixed with thioated dATP (AT hexamer+α-S-dATP) using Quant-It PicoGreen dsDNA Assay Kit are shown in Table 3. Only a single reaction for the RCA test condition including AT hexamers and α-S-dATP was performed instead of a duplicate reaction.

TABLE 3

Yield of RCA product DNA

| RCA test condition | Reaction #1 RCA DNA yield (ng/µL) | Reaction #2 RCA DNA yield (ng/µL) |
| --- | --- | --- |
| Random hexamer | 294.4 | 323.3 |
| AT hexamer | 548.2 | 563.4 |
| AT hexamer + α-S-dATP | 590.8 | — |

As presented in Table 3 and FIG. 2, the yield of RCA product DNA is increased when AT hexamer was used in comparison with the random hexamers. As illustrated in FIG. 2, the yield of the RCA product was approximately 55 µg when AT hexamers were used for the RCA reaction, whereas the yield of RCA product was approximately 28 µg when random hexamers were used for the RCA reaction. A similar high yield was observed when thioated bases were randomly incorporated into the RCA product after priming the amplification reaction with AT hexamers. Since coupled in vitro transcription and translation generally requires at least 1 microgram of template DNA, the higher DNA yield using AT hexamer primer in the RCA reactions enabled greater scale-up of subsequent transcription and translation.

Various DNA amplification products (samples) were generated for cell-free expression comparison in the forthcoming examples, as listed in Table 4. Table 4 also illustrates the different sequence parameters (e.g., presence or absence of transcription termination sequence) and/or modifications (e.g., presence or absence of thioated DNA, or codon usage) that are present in each template and the corresponding amplified nucleic acids, wherein "cc" denotes a contextual codon preference and "ic" denotes an individual codon preference.

TABLE 4

Characteristics of different amplification products (samples) used in the forthcoming examples.

| Sample No. | Encoding Gene | Amplification method | Transcription termination sequences | Modification | Template Sequence |
| --- | --- | --- | --- | --- | --- |
| 20 | EGFP | RCA | + | cc | Mini-circle of SEQ ID No. 1 |
| 22 | EGFP | RCA | − | cc | Mini-circle of SEQ ID No. 3 |
| 24 | EGFP | PCR | + | cc | SEQ ID No. 1 |
| 26 | EGFP | PCR | − | cc | SEQ ID No. 3 |
| 28 | EGFP | RCA | + | ic | Mini-circle of SEQ ID No. 2 |
| 30 | EGFP | RCA | − | ic | Mini-circle of SEQ ID No. 4 |
| 32 | EGFP | PCR | + | ic | SEQ ID No. 2 |
| 34 | EGFP | PCR | − | ic | SEQ ID No. 4 |
| 36 | EGFP | RCA | + | Thioated, amplified using AT hexamers; cc | Mini-circle of SEQ ID No. 5 |
| 38 | EGFP | RCA | + | non-thioated, amplified using AT hexamers; cc | Mini-circle of SEQ ID No. 5 |
| 40 | EGFP | RCA | + | non-thioated, amplified using random hexamers; cc | Mini-circle of SEQ ID No. 5 |
| 42 | EGFP | PCR | + | Non-thioated; cc | SEQ ID No. 5 |
| 44 | EGFP | RCA | − | Thioated, amplified using AT hexamers; cc | Mini-circle of SEQ ID No. 6 |

TABLE 4-continued

Characteristics of different amplification products (samples) used in the forthcoming examples.

| Sample No. | Encoding Gene | Amplification method | Transcription termination sequences | Modification | Template Sequence |
|---|---|---|---|---|---|
| 46 | EGFP | RCA | – | Non-thioated; amplified using AT hexamers; cc | Mini-circle of SEQ ID No. 6 |
| 48 | EGFP | PCR | – | Non-thioated; cc | SEQ ID No. 6 |
| 50 | IL-2 | RCA | + | cc | Mini-circle of SEQ ID No. 7 |
| 52 | IL-2 | PCR | + | cc | SEQ ID No. 7 |
| 54 | IL-2 | RCA | + | ic | Mini-circle of SEQ ID No. 8 |
| 56 | IL-2 | PCR | + | ic | SEQ ID No. 8 |
| 70 | EGFP | RCA | + | cc | Mini-circle of SEQ ID No. 1 |
| 72 | EGFP | RCA | + | cc | Plasmid of SEQ ID No. 1 (in pUC19) |
| 74 | EGFP | RCA | – | cc | Mini-circle of SEQ ID No. 3 |
| 76 | EGFP | RCA | – | cc | Plasmid of SEQ ID No. 3 (in pUC19) |

Example 2: Enhanced Protein Synthesis by Coupled In Vitro Transcription and Translation from RCA Product Protein expression by coupled in vitro transcription and translation was evaluated using the Expressway™ Mini Cell-Free Expression System (ThermoFisher Inc.), an E. coli-based coupled in vitro transcription and translation reaction that is suitable for linear and plasmid DNA templates. Per manufacturer specifications, the Expressway system requires a minimum concentration of DNA template of 148 ng/μL in order to add 1 microgram of template DNA into a 50 μL reaction. Synthesis of EGFP protein by coupled in vitro transcription and translation was compared among PCR amplified DNA and RCA products prepared from DNA-mini circles derived from SEQ ID No.1, SEQ ID No.2, SEQ ID No.3, or SEQ ID No.4. All of these sequences contain a gene coding for EGFP, but differ in several ways. For example, SEQ ID No.1 and SEQ ID No.2 comprise Class I/II transcription terminator sequences derived from terminator T1 of the E. coli rrnB operon, whereas SEQ ID No.3 and SEQ ID No.4 lack transcription termination sequences. Further, SEQ ID No.2 and SEQ ID No.4 include EGFP open reading frames that are codon-optimized according to the JCat tool [Grote et al., Nucleic Acids Res. 2005 Jul. 1; 33 (Web Server issue: W526-531). JCat: a novel tool to adapt codon usage of a target gene to its potential expression host], which maximizes individual codon usage of a target gene to the codon preferences of an expression host. SEQ ID No.1 and SEQ ID No.3 contain open reading frames for EGFP that are contextually adapted based on the following process: starting from the natural coding sequence of EGFP, only specific sites were re-coded to avoid cryptic start sites (ATG), cryptic ribosomal binding sites (AGGA, GAGG, GGAG), class II termination sequences [(A, C, or T)ATCTGTT], ribosomal slippery sequences [NNNYYY, where Y=(A, T)], and ribosomal pause sites (AGG, GGA, GAG. GGG, GGT, GTG) upstream of internal ATG methionines.

DNA mini-circles containing sequences SEQ ID No.1, SEQ ID No.2, SEQ ID No.3, and SEQ ID No.4 were prepared by ligation, and subsequently amplified by RCA with AT hexamers, as described in Example 1. Yield of the RCA product was quantified using Quant-It PicoGreen dsDNA Assay Kit (ThermoFisher Inc.). Approximately 1 microgram of RCA product derived from DNA mini-circle template was applied directly to Expressway Mini Cell-Free Expression reactions without any intermediate clean-up or purification steps. Further, there was no additional processing of the RCA product in terms of restriction digestion and/or ligation before its addition to the Expressway Mini Cell-Free Expression reactions. In separate cell-free expression reactions, 1 microgram of PCR amplified DNA with SEQ ID No.1, SEQ ID No.2, SEQ ID No.3, or SEQ ID No.4 (synthesized by GenScript via overlap extension PCR) were also tested, along with no template controls (NTC). All cell-free expression reactions were incubated at 30° C. for 6 hours with shaking (1200 rpm) in an Eppendorf Thermo-Mixer to synthesize the EGFP protein. The synthesized EGFP protein was allowed to fold into an active form by incubating it overnight at 4° C. prior to quantification by a fluorescence-based assay. The fluorescence of folded EGFP was measured from 10-fold dilutions of the expressed extract samples (in PBS) against a purified EGFP reference curve (BioVision, Inc.) using a SpectraMax® M5 Microplate Reader (Molecular Devices, LLC). Total EGFP yield from the in vitro transcription and translation was calculated in units of μg/mL.

The EGFP protein yield from RCA product DNA prepared from SEQ ID No.1 or PCR amplified DNA prepared from SEQ ID No.3 are depicted in FIG. 3. FIG. 3 illustrates that the EGFP expression was enhanced when RCA products 20 and 22 were employed for in-vitro transcription-translation in comparison to in-vitro transcription-translation reactions using PCR amplified DNA 24 and 26. FIG. 3 also shows that RCA product 22 yielded higher EGFP expression as compared to PCR-amplified DNA 26 even though the minimalistic expression sequence was devoid of any transcription termination sequences.

The EGFP protein yield from an in-vitro transcription-translation of an RCA product prepared from SEQ ID No.2 or a PCR amplified DNA prepared from SEQ ID No.4 are depicted in FIG. 4. As depicted in FIG. 4, the EGFP yield was much higher when RCA products 28, 30 were used for cell-free expression when compared to the PCR-amplified DNA 32, 34. FIG. 4 also shows that RCA product 30 resulted higher yield of EGFP compared to the PCR amplified DNA 34 even when the minimalistic expression sequence was devoid of transcription termination sequences. The higher yield of cell-free protein using an RCA product compared to PCR-amplified DNA was unexpected. In general, the transcription termination signals are required for the stability and/release of mRNA and for effective translation of the mRNA. For example, the protein expression from the PCR-amplified DNA 26 (FIG. 3) and 34 (FIG. 4) were substantially lower compared to the PCR-amplified DNA 24 (FIG. 3) and 32 (FIG. 4) respectively. The minimalistic expression sequences of the PCR amplified DNA 24 and 32 have Class I/II transcription terminators (as shown in FIGS. 3 and 4) and the minimalistic expression sequences of the PCR amplified DNA 26 and 34 lack transcription terminators. Thus, this data shows that RCA product derived from minimalistic DNA mini-circles improves protein expression by generating tandem repeats of cistronic mRNA species, wherein each cistron contains the mRNA for the desired target gene. The tandem repeats of the cistron may improve overall mRNA stability, particularly when transcription termination signals are absent, and thus contribute to higher translational flux of the desired protein product.

Example 3: Thioation of RCA Product Improves Protein Production in a Coupled In Vitro Transcription-Translation System Protein (EGFP) expression by coupled in vitro transcription and translation was evaluated using the Expressway Mini Cell-Free Expression System (ThermoFisher Inc) and PCR-amplified DNA or an RCA product. For these experiments, SEQ ID No. 5 and SEQ ID No. 6 were configured with a strong T7 gene10 translation enhancer sequence and T7 gene10 ribosome binding sequence that increase translation efficiency. Additionally, SEQ ID No. 5 includes a Class I transcription terminator (derived from T7 T-phi terminator sequence) which increases the termination efficiency depending on reaction conditions and the upstream DNA sequence elements. The EGFP coding region was optimized contextually and was identical between SEQ ID No. 5 and SEQ ID No. 6. DNA mini-circles were prepared by intramolecular ligation of each of the sequences, SEQ ID No.5 or SEQ ID No. 6. The ligated DNA mini-circles were subsequently amplified by RCA with random hexamers, AT hexamers, or AT hexamers in the presence or absence of thioated dATPs, as described in Example 1. RCA yield was quantified using Quant-It PicoGreen dsDNA Assay Kit (ThermoFisher). 0.5 micrograms of RCA product DNA were applied directly into Expressway Mini Cell-Free Expression reactions without any intermediate cleaning up steps. In separate cell-free expression reactions, 0.5 micrograms of PCR amplified DNA of SEQ ID No. 5 or SEQ ID No. 6 (synthesized by GenScript via overlap extension PCR) were also tested, along with no template controls (NTC). All cell-free expression reactions were incubated at 30° C. for 6 hours in an Eppendorf ThermoMixer (1200 rpm), and synthesized EGFP protein was allowed to fold overnight at 4° C. prior to fluorescence quantitation. The fluorescence of folded EGFP was measured from 100-fold dilutions of the extract samples (in PBS) against a purified EGFP reference curve (BioVision, Inc.) using a SpectraMax M5 Microplate Reader (Molecular Devices, LLC). Total EGFP yield was calculated in units of µg/mL.

EGFP protein yield from RCA products (including normal or thioated DNA derived from mini-circles prepared from SEQ ID No. 5) was compared against the yield from PCR-amplified DNA (prepared from SEQ ID No. 5, without thioation). As depicted in FIG. 5, the EGFP protein expression was much higher from RCA product 36 that was partially substituted with thioated nucleotides, compared to PCR-amplified DNA 42, or RCA products 38 and 40 that did not contain any thioated nucleotides.

Similarly, the expression yield of EGFP protein from SEQ ID No.6 was determined from RCA products (with or without thioation) compared to non-thioated PCR-amplified DNA. FIG. 6 shows the yield of EGFP was relatively higher for RCA product 44 that was partially substituted with thioated nucleotides, compared to the non-thioated RCA product 46 or a non-thioated PCR amplified template 48. For the PCR-amplified DNA 48, there was virtually no EGFP expression in the cell-free reaction (FIG. 6). Similar to the previous Example, this data confirms that transcription termination signals are required for effective translation of the mRNA, except when the minimalistic expression cassette is converted into RCA product.

Example 4: RNA Polymerase Run-Off Influences Protein Production in an In Vitro Transcription and Translation System Using an RCA Product in a Context-Dependent Manner Expression of PCR-amplified DNA or RCA product in an in vitro transcription and translation assay for human IL-2 was evaluated using the Expressway Mini Cell-Free Expression System (ThermoFisher Inc.). For these experiments, SEQ ID No. 7 and SEQ ID No. 8 (encoding IL-2 without a signal peptide) were created with Class/II transcriptional terminator sequences derived from terminator T1 of the *E. coli* rrnB operon. The minimalistic expression sequences of SEQ. ID. No. 7 and SEQ ID No. 8 were virtually identical except for codon usage within the IL-2 open reading frame. SEQ ID No.8 was codon-optimized according to the JCat tool which maximized individual codon usage of a target gene to the codon preferences of an expression host. SEQ ID No. 7 was contextually adapted based on the following process: starting from the natural coding sequence of human IL-2, only specific sites were re-coded to avoid cryptic start sites (ATG), cryptic ribosomal binding sites (AGGA, GAGG, GGAG), class II termination sequences [(A,C,T) ATCTGTT], ribosomal slippery sequences [NNNYYY, where Y=(A, T)], and ribosomal pause sites (AGG, GGA, GAG, GGG, GGT, GTG) upstream of internal ATG methionines. DNA mini-circles were prepared by intramolecular ligation of each of the DNA sequences, SEQ ID No. 7 and SEQ ID No.8. The mini-circles were subsequently amplified by RCA with AT hexamers, as described in Example 1. Yield of the RCA product was quantified using Quant-It PicoGreen dsDNA Assay Kit Assay Kit (ThermoFisher). 1 microgram of RCA DNA was applied directly into Expressway Mini Cell-Free Expression reactions without any intermediate clean-up step. In separate cell-free expression reactions, 1 microgram of PCR amplified DNA of SEQ ID No. 7 and SEQ ID No. 8 (synthesized by GenScript via overlap extension PCR) were also tested, along with no template controls (NTC). Each cell-free expression reaction additionally contained 2 μL of FluoroTect™ GreenLYS in vitro Translation Label (Promega) to randomly label nascent lysine residues (via anticodon UUU tRNA) with a fluorescent BODIPY-FL label. All cell-free expression reactions were incubated at 30° C. for 6 hours in an Eppendorf ThermoMixer (1200 rpm) and then kept overnight at 4° C. prior to analysis. Approximately 2 μL of cell-free expression reaction mixture was separated by SDS-PAGE and all translation products containing BODIPY-FL were detected by in-gel fluorescence using a Typhoon Variable Mode Imager (GE Healthcare). Fluorescent IL-2 bands (~16 kD) were digitally quantified using ImageJ software.

FIG. 7 demonstrates an SDS-PAGE gel for the IL-2 protein expressed using coupled in vitro transcription and translation. The expressed proteins were collected from cell-free expression reactions and loaded to SDS-PAGE for analysis. The proteins were separately expressed from RCA product 50 prepared from SEQ ID No.7, RCA product 54 prepared from SEQ ID No.8, PCR-amplified DNA 52 prepared from SEQ ID No.7, and PCR-amplified DNA 56 prepared from SEQ ID No.8. As depicted in FIG. 7, aside from background BODIPY-FL tRNA signal that was also present in NTC reactions (lane 2), fluorescent signal from SEQ ID No. 7 was predominately observed as ~16 kD translated IL-2 protein (lanes 3-4). In contrast, no IL-2 protein was observed for PCR-amplified DNA 56 (FIG. 7, lane 5). High-molecular weight proteins (26 kD-72 kD) were unexpectedly expressed using the RCA product 54 (SEQ ID No. 8), as shown in FIG. 7, lane 6. Lane 1 of FIG. 7 represents standard protein molecular weight marker (M). The reason might be the presence of two di-lysine repeats in the IL-2 sequence, which were re-coded into polyA tracts by the JCat tool because the AAA codon is significantly preferred over AAG in *E. coli*. These di-lysine repeats were not substantially re-coded in SEQ ID No. 7 by the contextual codon optimization process. AAAAAA tracts are often known as ribosomal slippery sequences that can potentially frameshift the translated product (Yan S et al.; 2015, Ribosome excursions during mRNA translocation mediate broad branching of frameshift pathways; *Cell*. 160: 870-81) and exert additional translational control through ribosomal stalling (Arthur et al., 2015, Translational control by lysine-encoding A-rich sequences; *Science Advances*. Vol. 1: No. 6: pg 1-11; e1500154).

FIG. 8 demonstrates the relative yield of 16 kD IL-2 protein from RCA product 50 (prepared from SEQ ID No.7), RCA product 54 (prepared from SEQ ID No.8), PCR-amplified DNA 52 (prepared from SEQ ID No.7), and PCR-amplified DNA 56 (prepared from SEQ ID No.8). FIG. 8 shows that the yield of IL-2 was increased when RCA product 50 was used for the cell-free expression compared to the PCR-amplified DNA 52. The data presented in FIGS. 7 and 8 also show that tandem repeats of cistronic mRNAs are generated from RCA product despite the presence of transcription termination sequences. The corresponding messages were effectively or ineffectively processed by ribosomes to affect cell-free protein yield, as long as the downstream cistrons in the message were designed appropriately.

Example 5: Protein Production in a Cell-Free Expression System Using an RCA Product Generated from a DNA Mini-Circle Compared to an RCA Product Generated from a Plasmid DNA Expression of EGFP in a cell-free system was compared among RCA products generated from DNA mini-circles consisting essentially of minimalistic expression sequences using either SEQ ID No. 1 (having Class I/11 transcriptional terminator sequence of the *E. coli* rrnB operon) or SEQ ID No. 3 (lacking a transcription terminator sequence). For these experiments, DNA mini-circles were prepared by intramolecular ligation of SEQ ID No. 1 or SEQ ID No. 3 as described in Example 1. For plasmid generation, SEQ ID No. 1 or SEQ ID No. 3 were ligated into the EcoRI and KpnI sites of pUC19, transfected into One Shot® TOP10 Chemically Competent *E. coli* (Invitrogen #C4040), and selected for ampicillin resistance. Individual plasmid clones were purified from *E. coli* using PureLink® HQ Mini Plasmid Purification Kit (Invitrogen #K2100-01) and verified by BamHI restriction digest. All DNA mini-circle and plasmid DNA templates were amplified by RCA with AT hexamers, as described in Example 1. RCA products were quantified using Quant-It PicoGreen dsDNA Assay Kit (ThermoFisher). 0.5 micrograms of RCA product DNA was applied directly into Expressway Mini Cell-Free Expression reactions without any intermediate clean-up. Cell-free expression reactions (including no template controls) were incubated at 30° C. for 5 hours in an Eppendorf Thermo-Mixer (1200 rpm), and synthesized EGFP protein was allowed to fold keeping at 4° C. for overnight prior to fluorescence quantitation. The fluorescence of folded EGFP was measured from 10-fold dilutions of the lysate samples (in PBS) against a purified EGFP reference curve (BioVision, Inc) using a SpectraMax M5 Microplate Reader (Molecular Devices, LLC). Total EGFP yield was calculated in units of μg/mL.

Yield of the EGFP protein from cell-free expression reactions that employed RCA products amplified from DNA mini-circles (70, 74) and RCA products of plasmid DNA (72, 76) are depicted in FIG. 9. The results show that the cell-free yield of EGFP is enhanced when RCA product is generated from DNA mini-circles rather than plasmid DNA. Further, EGFP can be expressed even in the absence of transcription termination sequences using RCA product derived from DNA mini-circles (74) compared to RCA product derived from plasmid (76). This data shows that various intervening sequences, such as origin of replication, antibiotic selection sequence and extraneous sequences involved in clone screening, that are present in the RCA product generated from a plasmid DNA can impair cell-free expression of the desired protein target. In contrast, beneficial and productive run-off can occur when the RCA concatemer is generated from a DNA mini-circle consisting essentially of a minimalistic expression sequence, even in the absence of a transcription termination (which generally destabilizes mRNA transcripts).

The foregoing examples are illustrative of some features of the invention, and are selected embodiments from a manifold of all possible embodiments. The invention may be embodied in other specific forms without departing from the spirit or essential characteristics thereof. While only certain features of the invention have been illustrated and described herein, one skilled in the art, given the benefit of this disclosure, will be able to make modifications/changes to optimize the parameters. The foregoing embodiments are therefore to be considered in all respects as illustrative rather than limiting on the invention described herein. Where necessary, ranges have been supplied, and those ranges are inclusive of all sub-ranges there between.

The invention claimed is:

1. A method for in vitro transcription comprising:
generating a ribonucleic acid (RNA) in a cell-free transcription reaction from a double-stranded rolling circle amplification (RCA) product comprising tandem repeats of a minimalistic deoxyribonucleic acid (DNA) sequence of interest,
wherein the minimalistic DNA sequence of interest comprises a promoter sequence and an RNA coding region,
wherein the DNA sequence of interest is devoid of a transcription termination sequence, and
wherein the double-stranded RCA product is devoid of any extraneous sequences that are required for propagation of a plasmid in a host cell.

2. The method of claim 1, wherein the promoter sequence is located upstream of the RNA coding region in the DNA sequence of interest.

3. The method of claim 1, wherein the DNA sequence of interest further comprises an insulator sequence.

4. The method of claim 1, wherein the DNA sequence of interest further comprises a purification tag sequence.

5. The method of claim 1, wherein the DNA sequence of interest is a codon-optimized sequence for enhancing RNA stability.

6. The method of claim 1, wherein the generated RNA comprises tandem repeats of cistronic RNA species, wherein each cistronic RNA species comprises an RNA sequence coded by the DNA sequence of interest.

7. The method of claim 1, wherein the double-stranded RCA product comprises a thioated nucleotide.

8. The method of claim 1, wherein the cell-free transcription reaction is performed using a prokaryotic cell extract, a eukaryotic cell extract, or a combination thereof.

9. A method for in vitro transcription, comprising:
generating a double-stranded rolling circle amplification (RCA) product via rolling circle amplification of a deoxyribonucleic acid (DNA) mini-circle comprising a minimalistic DNA sequence of interest; and
generating a ribonucleic acid (RNA) in a cell-free transcription reaction from the double-stranded RCA product,
wherein the minimalistic DNA sequence of interest comprises a promoter sequence and an RNA coding region,
wherein the DNA sequence of interest is devoid of a transcription termination sequence, and
wherein the DNA mini-circle is devoid of any extraneous sequences that are required for propagation of a plasmid in a host cell.

10. The method of claim 9, wherein the double-stranded RCA product is used in the cell-free transcription reaction without any further processing.

11. The method of claim 9, wherein the double-stranded RCA product comprises a thioated nucleotide.

12. The method of claim 9, wherein the cell-free transcription reaction is performed using a prokaryotic cell extract, a eukaryotic cell extract, or a combination thereof.

13. The method of claim 9, wherein the DNA sequence of interest further comprises an insulator sequence.

14. The method of claim 9, wherein the DNA sequence of interest further comprises a purification tag sequence.

15. The method of claim 9, wherein the DNA sequence of interest is a codon-optimized sequence for enhancing RNA stability.

16. The method of claim 9, wherein the generated RNA comprises tandem repeats of cistronic RNA species, wherein each cistronic RNA species comprises an RNA sequence coded by the DNA sequence of interest.

17. The method of claim 9, wherein the rolling circle amplification is performed using a final concentration of deoxyribonucleoside triphosphates (dNTPs) in a range of 10 μM to 10 mM.

18. The method of claim 9, wherein the rolling circle amplification is performed using a random primer mixture comprising a nucleotide analogue, and wherein the nucleotide analogue is an inosine, a Locked Nucleic Acid (LNA) nucleotide, a Peptide Nucleic Acid (PNA) nucleotide, a thioated nucleotide, 2-amino-deoxyadenosine, 2-thio-deoxythymidine, a polycation nucleotide, or a Zip Nucleic Acid (ZNA) polycation modified nucleotide.

19. The method of claim 18, wherein the random primer mixture has a sequence +N+N(atN)(atN)(atN)*N.

* * * * *

SEQUENCE LISTING

<160> NUMBER OF SEQ ID NOS: 10

<210> SEQ ID NO 1
<211> LENGTH: 970
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
ccggaattcg gatccgaaat taatacgact cactataggg agaccacaac ggtttccctc    60
tagcgtaagg aggtttggaa tgcatcacca tcaccatcac ggctcactgg aagttctgtt   120
ccaggggccc ggctcagtaa gcaagggcga agagctgttc accggggttg tgcccatcct   180
ggtcgagctg gacggcgacg taaacggcca caagttcagc gtgtccggcg aaggcgaagg   240
cgacgccacc tacggcaagc tgaccctgaa gttcatctgc accaccggca agctgcccgt   300
gcccctggccc accctcgtga ccaccctgac ctacggcgtg cagtgcttca gccgctaccc   360
cgaccacatg aagcagcacg acttcttcaa atccgccatg cccgaaggct acgtccaaga   420
gcgcaccatc ttcttcaaag acgacggcaa ctacaagacc cgcgccgaag tgaagttcga   480
aggcgacacc ctggtgaacc gcatcgagct gaagggcatc gacttcaaag aagacggcaa   540
catcctgggg cacaagctcg agtacaacta caacagccac aacgtctata tcatggccga   600
caagcagaag aacggcatca aggtgaactt caagatccgc cacaacatcg aagacggcag   660
cgtgcagctc gccgaccact accagcagaa cacccccatc ggcgacggcc ccgtgctgct   720
gcccgacaac cactacctga gcacccagtc cgccctgagc aaagaccccca acgaaaagcg   780
cgatcacatg gtcctgctcg agttcgtgac cgccgccggc atcactctcg gcatggacga   840
gctgtacaag taataatact agagccaggc atcaaataaa acgaaaggct cagtcgaaag   900
actgggcctt tcgttttatc tgttgtttgt cggtgaacgc tctctactag agcgcggatc   960
cggtaccccg                                                          970
```

<210> SEQ ID NO 2
<211> LENGTH: 970
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
ccggaattcg gatccgaaat taatacgact cactataggg agaccacaac ggtttccctc    60
tagcgtaagg aggtttggaa tgcatcatca ccatcaccac ggctcactgg aagttctgtt   120
ccaggggccc ggctcagttt ctaaaggtga agaactgttc accggtgttg ttccgatcct   180
ggttgaactg gacggtgacg ttaacggtca caaattctct gtttctggtg aaggtgaagg   240
tgacgctacc tacggtaaac tgaccctgaa attcatctgc accaccggta actgccggt   300
tccgtggccg accctggtta ccaccctgac ctacggtgtt cagtgcttct ctcgttaccc   360
ggaccacatg aaacagcacg acttcttcaa atctgctatg ccggaaggtt acgttcagga   420
acgtaccatc ttcttcaaag acgacggtaa ctacaaaacc cgtgctgaag ttaaattcga   480
aggtgacacc ctggttaacc gtatcgaact gaaaggtatc gacttcaaag aagacggtaa   540
catcctgggt cacaaactgg aatacaacta caactctcac aacgtttaca tcatggctga   600
caaacagaaa aacggtatca agttaacttc aaaatccgt cacaacatcg aagacggttc   660
```

```
tgttcagctg gctgaccact accagcagaa cacccgatc ggtgacggtc cggttctgct      720
gccggacaac cactacctgt ctacccagtc tgctctgtct aaagacccga acgaaaaacg      780
tgaccacatg gttctgctgg aatttgttac cgctgctggt atcaccctgg gtatggacga      840
actgtacaaa taataatact agagccaggc atcaaataaa acgaaaggct cagtcgaaag      900
actgggcctt tcgttttatc tgttgtttgt cggtgaacgc tctctactag agcgcggatc      960
cggtaccccg                                                             970

<210> SEQ ID NO 3
<211> LENGTH: 882
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ccggaattcg gatccgaaat taatacgact cactataggg agaccacaac ggtttccctc       60
tagcgtaagg aggtttggaa tgcatcacca tcaccatcac ggctcactgg aagttctgtt      120
ccaggggccc ggctcagtaa gcaagggcga agagctgttc accggggttg tgcccatcct      180
ggtcgagctg gacggcgacg taaacggcca agttcagc gtgtccggcg aaggcgaagg       240
cgacgccacc tacggcaagc tgaccctgaa gttcatctgc accaccggca agctgcccgt      300
gccctggccc accctcgtga ccaccctgac ctacggcgtg cagtgcttca gccgctaccc      360
cgaccacatg aagcagcacg acttcttcaa atccgccatg cccgaaggct acgtccaaga      420
gcgcaccatc ttcttcaaag acgacggcaa ctacaagacc cgcgccgaag tgaagttcga      480
aggcgacacc ctggtgaacc gcatcgagct gaagggcatc gacttcaaag aagacggcaa      540
catcctgggg cacaagctcg agtacaacta caacagccac aacgtctata tcatggccga      600
caagcagaag aacggcatca aggtgaactt caagatccgc cacaacatcg aagacggcag      660
cgtgcagctc gccgaccact accagcagaa cacccccatc ggcgacggcc ccgtgctgct      720
gcccgacaac cactacctga gcacccagtc cgccctgagc aaagaccccca acgaaaagcg      780 cgatcacatg gtcctgctcg agttcgtgac cgccgccggc atcactctcg gcatggacga      840
gctgtacaag taataatact agagcgcgga tccggtaccc cg                         882

<210> SEQ ID NO 4
<211> LENGTH: 882
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
ccggaattcg gatccgaaat taatacgact cactataggg agaccacaac ggtttccctc       60
tagcgtaagg aggtttggaa tgcatcatca ccatcaccac ggctcactgg aagttctgtt      120
ccaggggccc ggctcagttt ctaaaggtga agaactgttc accggtgttg ttccgatcct      180
ggttgaactg gacggtgacg ttaacggtca caattctct gtttctggtg aaggtgaagg       240
tgacgctacc tacggtaaac tgaccctgaa attcatctgc accaccggta aactgccggt      300
tccgtggccg accctggtta ccaccctgac ctacggtgtt cagtgcttct ctcgttaccc      360
ggaccacatg aaacagcacg acttcttcaa atctgctatg ccggaaggtt acgttcagga      420
```

```
acgtaccatc ttcttcaaag acgacggtaa ctacaaaacc cgtgctgaag ttaaattcga    480
aggtgacacc ctggttaacc gtatcgaact gaaaggtatc gacttcaaag aagacggtaa    540
catcctgggt cacaaactgg aatacaacta caactctcac aacgtttaca tcatggctga    600
caaacagaaa aacggtatca agttaacttc aaaatccgt cacaacatcg aagacggttc     660
tgttcagctg gctgaccact accagcagaa caccccgatc ggtgacggtc cggttctgct    720
gccggacaac cactacctgt ctacccagtc tgctctgtct aaagacccga acgaaaaacg    780
tgaccacatg gttctgctgg aatttgttac cgctgctggt atcaccctgg gtatggacga    840
actgtacaaa taataatact agagcgcgga tccggtaccc cg                       882

<210> SEQ ID NO 5
<211> LENGTH: 939
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
ccgggatcct tctttaaatt aatacgactc actataggga gaccacaacg gtttccctct     60
agaaataatt ttgtttaact ttaagaagga gatatacata tgcatcacca tcaccatcac    120
ggctcactgg aagttctgtt ccaggggccc ggctcagtaa gcaagggcga agagttgttt    180
accggggttg tgccgatcct tgtcgagctt gacggcgacg taaacggcca caagtttagc    240
gtgtccggcg aaggcgaagg cgacgcaacg tacggcaagc ttacgcttaa gtttatctgc    300
acgacgggca agcttccggt gccgtggccg acgcttgtga cgacgcttac gtacggcgtg    360
cagtgcttta gccgctaccc agatcacatg aagcaacacg atttctttaa gtccgcaatg    420
cccgaaggct acgtccaaga gcgcacgatc ttcttcaaag acgacggcaa ctacaagacg    480
cgcgcagaag tgaagtttga aggcgatacg cttgtgaacc gcatcgagct taagggcatc    540
gatttcaaag aagacggcaa catccttggg cacaagcttg agtacaacta caacagccac    600
aacgtctata tcatggcaga taagcaaaag aacggcatca aggtgaactt taagatccgc    660
cacaacatcg aagacggcag cgtgcaactt gcagatcact accaacaaaa cacgccgatc    720
ggcgacggcc cggtgcttct tccggataac cactacctta gcacgcaatc cgcacttagc    780
aaagatccga acgaaaagcg cgatcacatg gtccttcttg agtttgtgac ggcagccggc    840
atcacgcttg gcatggacga gctttacaag taataactag cataacccct tggggcctct    900
aaacgggtct tgaggggttt tttgctgcag agatctccg                           939

<210> SEQ ID NO 6
<211> LENGTH: 891
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
ccgggatcct tctttaaatt aatacgactc actataggga gaccacaacg gtttccctct     60
agaaataatt ttgtttaact ttaagaagga gatatacata tgcatcacca tcaccatcac    120
ggctcactgg aagttctgtt ccaggggccc ggctcagtaa gcaagggcga agagttgttt    180
accggggttg tgccgatcct tgtcgagctt gacggcgacg taaacggcca caagtttagc    240
gtgtccggcg aaggcgaagg cgacgcaacg tacggcaagc ttacgcttaa gtttatctgc    300
```

```
acgacgggca agcttccggt gccgtggccg acgcttgtga cgacgcttac gtacggcgtg      360
cagtgcttta gccgctaccc agatcacatg aagcaacacg atttctttaa gtccgcaatg      420
cccgaaggct acgtccaaga gcgcacgatc ttcttcaaag acgacggcaa ctacaagacg      480
cgcgcagaag tgaagtttga aggcgatacg cttgtgaacc gcatcgagct taagggcatc      540
gatttcaaag aagacggcaa catccttggg cacaagcttg agtacaacta caacagccac      600
aacgtctata tcatggcaga taagcaaaag aacggcatca aggtgaactt taagatccgc      660
cacaacatcg aagacggcag cgtgcaactt gcagatcact accaacaaaa cacgccgatc      720
ggcgacggcc cggtgcttct tccggataac cactaccta gcacgcaatc cgcacttagc      780
aaagatccga acgaaaagcg cgatcacatg gtccttcttg agtttgtgac ggcagccggc      840
atcacgcttg gcatggacga gctttacaag taataactgc agagatctcc g      891
```

<210> SEQ ID NO 7
<211> LENGTH: 655
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
ccggaattcg gatccgaaat taatacgact cactataggg agaccacaac ggtttccctc      60
tagcgtaagg aggtttggaa tgcatcacca tcaccatcac ggctcactgg aagttctgtt     120
ccaggggccc ggctcagcac ctacttcaag ttctacaaag aaaacacagc tacaactcga     180
gcatttactg ctcgatttac agatgatttt gaacggcatt aataattaca agaatcctaa     240 actcaccccgc atgctcacat ttaagtttta catgcccaag aaggccacag aactgaaaca     300
tcttcagtgt ctagaagaag aactcaaacc tctggaagaa gtgctcaact tagctcaaag     360
caaaaacttt cacttaagac ccagggactt aatcagcaat atcaacgtaa tagttctcga     420
actaaaaggc tctgaaacaa cattcatgtg tgaatacgct gacgagacag caaccattgt     480
agaatttctg aaccgttgga ttaccttttg tcaaagcatc atctcaacac tgacttaata     540
atactagagc caggcatcaa ataaaacgaa aggctcagtc gaaagactgg gcctttcgtt     600
ttatctgttg tttgtcggtg aacgctctct actagagcgc ggatccggta ccccg         655
```

<210> SEQ ID NO 8
<211> LENGTH: 655
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
ccggaattcg gatccgaaat taatacgact cactataggg agaccacaac ggtttccctc      60
tagcgtaagg aggtttggaa tgcatcatca ccatcaccac ggctcactgg aagttctgtt     120
ccaggggccc ggctcagctc cgacctcttc ttctaccaaa aaacccagc tgcagctgga     180 acacctgctg ctggacctgc agatgatcct gaacggtatc aacaactaca aaacccgaa     240 actgacccgt atgctgacct tcaaattcta catgcccaaa aaagctaccg aactgaaaca     300
cctgcagtgc ctggaagaag aactgaaacc gctggaagaa gttctgaacc tggctcagtc     360
taaaaacttc cacctgcgtc cgcgtgacct gatctctaac atcaacgtta tcgttctgga     420
```

```
actgaaaggt tctgaaacca ccttcatgtg cgaatacgct gacgaaaccg ctaccatcgt    480
tgaatttctg aaccgttgga tcaccttctg ccagtctatc atctctaccc tgacctaata    540
atactagagc caggcatcaa ataaaacgaa aggctcagtc gaaagactgg gcctttcgtt    600
ttatctgttg tttgtcggtg aacgctctct actagagcgc ggatccggta ccccg        655

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 9

His His His His His His
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Tyr Lys Asp Asp Asp Asp Lys
1               5
```